US010533969B2

United States Patent
Omura et al.

(10) Patent No.: US 10,533,969 B2
(45) Date of Patent: Jan. 14, 2020

(54) METHOD FOR PREDICTING IRON LOSS OF NON-ORIENTED ELECTRICAL STEEL SHEET AFTER SHEARING

(71) Applicant: JFE STEEL CORPORATION, Chiyoda-ku, Tokyo (JP)

(72) Inventors: Takeshi Omura, Tokyo (JP); Yoshiaki Zaizen, Tokyo (JP); Kunihiro Senda, Tokyo (JP)

(73) Assignee: JFE STEEL CORPORATION, Chiyoda-ku, Tokyo (JP)

( * ) Notice: Subject to any disclaimer, the term of this patent is extended or adjusted under 35 U.S.C. 154(b) by 282 days.

(21) Appl. No.: 15/521,406

(22) PCT Filed: Nov. 2, 2015

(86) PCT No.: PCT/JP2015/005510
§ 371 (c)(1),
(2) Date: Apr. 24, 2017

(87) PCT Pub. No.: WO2016/072088
PCT Pub. Date: May 12, 2016

(65) Prior Publication Data
US 2017/0315093 A1    Nov. 2, 2017

(30) Foreign Application Priority Data
Nov. 4, 2014    (JP) .................... 2014-224461

(51) Int. Cl.
*G01N 27/72*    (2006.01)
*G01R 33/12*    (2006.01)

(52) U.S. Cl.
CPC ............. *G01N 27/72* (2013.01); *G01R 33/12* (2013.01)

(58) Field of Classification Search
CPC ............ G01N 27/72; G01R 33/12; H01F 1/16
USPC ........................................................ 148/320
See application file for complete search history.

(56) References Cited

FOREIGN PATENT DOCUMENTS

| JP | 2003240831 A | 8/2003 |
|---|---|---|
| JP | 2005300211 A | 10/2005 |
| JP | 2011019398 A | 1/2011 |
| WO | 2014128938 A1 | 8/2014 |

OTHER PUBLICATIONS

NPL-1: English translation of Kawabe et al, Estimation of deteriorated magnetic properties of non-oriented electrical steel sheets due to cutting stress, Journal of the Magnetic Society of Japan, vol. 38, No. 1, pp. 5-10 (Jan. 2014), (Year: 2014).*

(Continued)

*Primary Examiner* — Jie Yang
(74) *Attorney, Agent, or Firm* — Kenja IP Law PC

(57) ABSTRACT

To predict the iron loss of a non-oriented electrical steel sheet after shearing, a non-oriented electrical steel sheet is sheared to a certain width, and iron loss $Wt(B_0)$ of the non-oriented electrical steel sheet after shearing is estimated according to a predetermined relational expression based on iron loss $Wn(B_1)$ in a non-machining-affected zone in which no machining strain is introduced by the shearing and iron loss $Wi(B_2)$ in a machining affected zone in which machining strain is introduced.

10 Claims, 14 Drawing Sheets

(56) References Cited

OTHER PUBLICATIONS

Dec. 28, 2018, Office Action issued by the State Intellectual Property Office in the corresponding Chinese Patent Application No. 201580059492.4 with English language search report.
Dec. 8, 2015, International Search Report issued in the International Patent Application No. PCT/JP2015/005510.
Morio Kawabe et al., "Estimation of Deteriorated Magnetic Properties of Non-oriented Electrical Steel Sheets due to Cutting Stress", Journal of the Magnetics Society of Japan, vol. 38, No. 1, Jan. 1, 2014, pp. 5-10.
Tetsuya Aoki et al., "Magnetic Field Simulation for Development of Products Using Magnetic Circuits", DENSO Technical Review, vol. 12, No. 2, 2007, pp. 129-135.
Yoshiyuki Kashiwara et al., "Estimation Model for Magnetic Properties of Stamped Electrical Steel Sheet", Journal of the Institute of Electrical Engineers of Japan, vol. 131, No. 7, 2011, pp. 567-574.
Jun. 20, 2017, Notification of Reasons for Refusal issued by the Japan Patent Office in the corresponding Japanese Patent Application No. 2014-224461 with English language concise statement of relevance.
Aug. 22, 2017, the Extended European Search Report issued by the European Patent Office in the corresponding European Patent Application No. 15857476.4.
Kunihiro Senda et al., Influence of shearing process on domain structure and magnetic properties of non-oriented electrical steel, Journal of Magnetism and Magnetic Materials, 2006, pp. e513-e515, vol. 304, No. 2.
T. Nakata et al., Effects of Stress Due to Cutting on Magnetic Characteristics of Silicon Steel, IEEE Translation Journal on Magnetics in Japan, Jun. 1992, pp. 453-457, vol. 7, No. 6.
May 3, 2018, Office Action issued by the Korean Intellectual Property Office in the corresponding Korean Patent Application No. 10-2017-7014879 with English language Concise Statement of Relevance.

* cited by examiner

Electric discharge machining

Total non-machining-affected width : 30 mm

Shear cutting

Total non-machining-affected width : 30−6*1.5=21 mm
Total machining affected width : 6*1.5=9 mm

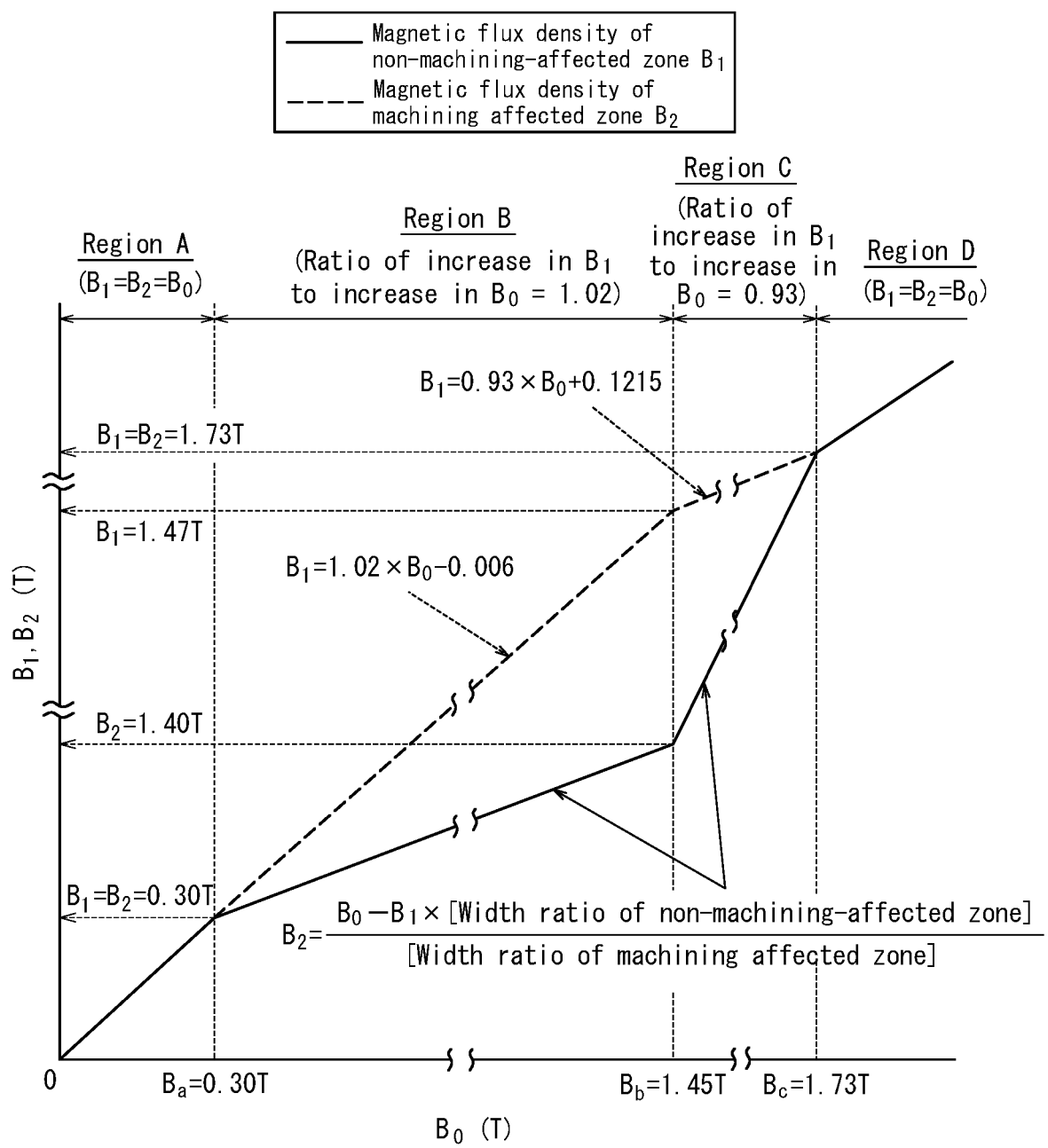

METHOD FOR PREDICTING IRON LOSS OF NON-ORIENTED ELECTRICAL STEEL SHEET AFTER SHEARING

TECHNICAL FIELD

This disclosure relates to a technique of utilizing non-oriented electrical steel sheets for iron core materials of motors and the like, and more particularly to methods for predicting iron loss of non-oriented electrical steel sheets after shearing.

BACKGROUND

Non-oriented electrical steel sheets used for iron cores of motors and the like are subjected to forming processes including shearing, such as shear cutting and punching, for increasing productivity. In this case, plastic strain and elastic strain are introduced to the steel sheets during shearing, causing an increase in iron loss.

In particular, in the case of core size being small and the steel sheet having a small width after subjection to shearing, deterioration of iron loss properties due to strain is quite conspicuous and the actual iron loss results are greatly different from those obtained with an evaluation method prescribed in a JIS standard, which fact causes a problem of not being able to obtain motor properties as designed.

In general, to predict motor properties with high accuracy at the design stage, it is necessary in the analysis of electromagnetic field and the like to use iron loss properties that take into account the influence of shearing. As such a method for simulating iron loss properties taking into consideration the influence of shearing, for example, *DENSO Technical Review*, vol. 12, No. 2, 2007, pp. 129-135 (NPL 1) describes a technique of actually measuring the iron loss after shearing and incorporating the measurements into the simulation, and *Journal of the Institute of Electrical Engineers of Japan*, Vol. 131, No. 7, 2011, pp. 567-574 (NPL 2) describes a technique of predicting the iron loss of a single plate under tensile and compressive stress in combination with the amount of strain determined by elasto-plastic deformation analysis.

CITATION LIST

Non-Patent Literature

NPL 1: *DENSO Technical Review*, vol. 12, No. 2, 2007, pp. 129-135
NPL 2: *Journal of the Institute of Electrical Engineers of Japan*, Vol. 131, No. 7, 2011, pp. 567-574

SUMMARY

Technical Problem

These techniques, however, require measurement of actual iron loss for steel strips of all possible widths available in shearing as well as complicated elasto-plastic deformation analysis, and are thus very time consuming, labor intensive, and costly. Therefore, it is difficult to use these techniques to meet every actual design specification, and the need for simplified prediction of iron loss still remains very high.

It could thus be helpful to provide a method for predicting, in a simplified and highly accurate manner, iron loss properties of a non-oriented electrical steel sheet that is sheared to a certain width.

As used herein, the term "shearing" refers to broadly-construed shear processing including, for example, shear cutting and punching, which involves cutting a steel sheet as a material to be worked to the desired shape and dimensions by causing plastic deformation (shearing deformation) and eventually rupture of the steel sheet.

Solution to Problem

To that end, we engaged in intensive studies and made the following discoveries.

(1) A non-oriented electrical steel sheet after shearing contains a non-machining-affected zone in which no machining strain is introduced, and a machining affected zone in which machining strain is introduced, and the iron loss of the non-oriented electrical steel sheet can be predicted by summing up iron loss in the non-machining-affected zone and iron loss in the machining affected zone according to the proportions of the non-machining-affected zone and the machining affected zone.

(2) Magnetic flux flowing in the non-machining-affected zone and in the machining affected zone can be roughly classified into three models (regions) given below according to the mean magnetic flux density.

Region 1: A region in which as mean magnetic flux density $B_0$ increases, magnetic flux density of the non-machining-affected zone $B_1$ and magnetic flux density of the machining affected zone $B_2$ increase at the same rate.

Region 2: A region in which as mean magnetic flux density $B_0$ increases, magnetic flux density of the non-machining-affected zone $B_1$ increases at a higher rate than magnetic flux density of the machining affected zone $B_2$.

Region 3: A region in which as mean magnetic flux density $B_0$ increases, magnetic flux density of the machining affected zone $B_2$ increases at a higher rate than magnetic flux density of the non-machining-affected zone $B_1$.

Here, $B_0$, $B_1$, and $B_2$ denote a mean magnetic flux density of the non-oriented electrical steel sheet after shearing, a magnetic flux density of the non-machining-affected zone, and a magnetic flux density of the machining affected zone, respectively, upon excitation after the shearing.

(3) In these models, for example, by setting iron loss in the non-machining-affected zone and iron loss in the machining affected zone as described below, it becomes possible to predict iron loss of a non-oriented electrical steel sheet sheared to an arbitrary width in a simpler way with high accuracy over the conventional techniques.

- An estimation is made of iron loss of a sample of the same material as the steel sheet to be predicted with a small degree of influence exerted by shearing, such as a sample having a relatively large width after subjection to shearing or a sample subjected to electric discharge machining with little influence of strain, and the result is used as the iron loss in the non-machining-affected zone.
- A comparison is made of iron loss of samples of the same material but with different degrees of influence exerted by shearing (for example, compare iron loss of a sample subjected to electric discharge machining with that of a sample shear-cut (sheared) to an arbitrary width, or compare iron loss of two samples shear-cut to different widths), to thereby derive the iron loss in the machining affected zone.

It is to be noted that the iron loss in the machining affected zone may be substituted by iron loss as measured upon a uniaxial compressive stress of 100 MPa or more being applied to a non-oriented electrical steel sheet of the same material as the steel sheet to be predicted.

(4) To determine the strain introduction width from a machined edge, although it is optimal to use the results measured using X-rays or synchrotron radiation, in a simplified setup, it is possible to obtain a practically reasonable prediction accuracy level by using a value that is two to four times the sheet thickness.

The following provides a description of experiments leading to these discoveries.

Experiment 1

A non-oriented electrical steel sheet having a thickness of 0.20 mm to 0.65 mm was shear-cut (sheared) to obtain a sample of 30 mm in width. From the 30-mm wide sample, four Epstein test pieces (hereinafter, also referred to simply as "test pieces") were prepared, each being 30-mm wide and 280-mm long. In this case, shear cutting was performed so that the rolling direction coincided with the longitudinal direction of each test piece.

Then, the residual stress distribution at an edge of the sample was measured by X-ray diffraction. In this case, stress was derived from measurements with the iso-inclination method and calculations with the half-value breadth method. FIG. 1A illustrates the stress measurement results for a sample with a thickness of 0.50 mm. FIG. 1B illustrates the stress measurement procedure.

It can be seen from FIG. 1A that strain is present (machining influence extends) up to about 1.5 mm from the machined edge of the sample.

In addition, FIG. 2 illustrates the relationship between the sheet thickness of each sample and the distance from the machined edge over which the machining influence extends (this distance will also be referred to as "machining affected width"). It can be seen from FIG. 2 that the machining affected width varies with the sheet thickness of the sample.

Then, in accordance with the sheet thickness of the sample, holes were machined to a diameter of 0.5 mm at 0.5 to 2.2 mm from both ends, and the probe coil was passed through the holes to measure the magnetic flux density distribution of a non-machining-affected zone at the widthwise central portion of the sample and the magnetic flux density distribution of a machining affected zone near the machined edge.

FIG. 3 illustrates the relationship between $B_0$ and $B_1$, $B_2$, where $B_0$ denotes the mean magnetic flux density of a sample having a sheet thickness of 0.5 mm upon excitation, $B_1$ denotes the magnetic flux density of a non-machining-affected zone at the widthwise central portion of the sample, and $B_2$ denotes the magnetic flux density of the machining affected zone near the machined edge.

As illustrated in FIG. 3, in Region A in which mean magnetic flux density $B_0$ ranges up to about 0.3 T, the machining affected zone and the non-machining-affected zone have substantially identical magnetic flux flows. In Region B in which mean magnetic flux density $B_0$ ranges from about 0.3 T to about 1.4 T, it is easy for the magnetic flux to flow in the non-machining-affected zone in relation to mean magnetic flux density $B_0$, and the ratio of increase in magnetic flux density of the non-machining-affected zone $B_1$ to increase in mean magnetic flux density $B_0$ was determined to be 1.015.

Further, in Region C in which mean magnetic flux density $B_0$ ranges from about 1.4 T to about 1.7 T, it is difficult for the magnetic flux to flow in the non-machining-affected zone in relation to mean magnetic flux density $B_0$, and the ratio of increase in magnetic flux density of the non-machining-affected zone $B_1$ to increase in mean magnetic flux density $B_0$ was determined to be 0.93.

Eventually at a point where mean magnetic flux density $B_0$ reached 1.7 T, the magnetic flux density of the machining affected zone matched the magnetic flux density of the non-machining-affected zone, and in Region D in which mean magnetic flux density $B_0$ is greater than 1.7 T, the machining affected zone and the non-machining-affected zone showed an identical magnetic flux density.

The upper limit, $B_a$, for the mean magnetic flux density (i.e., a mean magnetic flux density representative of a boundary value between Region A and Region B) showed sheet thickness dependence in Region A in which the machining affected zone and the non-machining-affected zone have substantially identical magnetic flux flows. It can be seen from FIG. 4 that $B_a$ varied with the sheet thickness for samples having a sheet thickness of 0.25 mm to 0.50 mm, and remained constant for samples having a sheet thickness of less than 0.25 mm and more than 0.50 mm.

As to the upper limit (boundary value) for the mean magnetic flux density in each region other than Region A, no sheet thickness dependence was observed. The ratio of increase in magnetic flux density of the non-machining-affected zone $B_1$ to increase in mean magnetic flux density $B_0$ in Region B, and alternatively to that in Region C, was determined to be about 1.02 and about 0.93 on average for all the samples, respectively. Further, the upper limit, $B_b$, for the mean magnetic flux density in Region B (a mean magnetic flux density representative of a boundary value between Region B and Region C) was determined to be about 1.45 T on average for all the samples.

In view of the measurement results, we developed a model as illustrated in FIG. 5, with the following principles:
(a) As illustrated in FIG. 4, the upper limit $B_a$ for the region (Region A) in which the machining affected zone and the non-machining-affected zone have substantially identical magnetic flux flows is set to 0 T when the sheet thickness t is 0.25 mm or less, 1.2*t−0.3 when the sheet thickness t is more than 0.25 mm and 0.50 mm or less, and 0.3 T when the sheet thickness t is greater than 0.50 mm;
(b) In the region (Region B) in which it is easy for the magnetic flux to flow in the non-machining-affected zone in relation to the mean magnetic flux density, the ratio of increase in magnetic flux density of the non-machining-affected zone $B_1$ to increase in mean magnetic flux density $B_0$, which ratio represents the easiness of flow of magnetic flux into the non-machining-affected zone, is set to 1.02;
(c) In the region (Region C) in which it is difficult for the magnetic flux to flow in the non-machining-affected zone in relation to the mean magnetic flux density, the ratio of increase in magnetic flux density of the non-machining-affected zone $B_1$ to increase in mean magnetic flux density $B_0$, which ratio represents the easiness of flow of magnetic flux into the non-machining-affected zone, is set to 0.93; and
(d) The upper limit $B_b$ for the mean magnetic flux density in the region (Region B) in which it is easy for the magnetic flux to flow in the non-machining-affected zone in relation to the mean magnetic flux density (i.e., a mean magnetic flux density representative of a boundary value between Region B and Region C) is set to 1.45 T.

We investigated the accuracy of this model.

Experiment 2

The 0.5-mm thick non-oriented electrical steel sheet used in Experiment 1 was cut into a sample of 10 mm wide and 280 mm long. As used herein, "machining affected width" refers to the distance from the machined edge over which the machining influence extends, and "non-machining-affected width" refers to the width of a region over which no machining influence is exerted. It is to be noted that the cutting process was shear cutting (shearing) or electric discharge machining.

Then, as illustrated in FIGS. 6A and 6B, three samples were cut out from the steel sheet through the same process, and were combined into a test piece having a total width of 30 mm. In this way, four test pieces were prepared with their longitudinal direction parallel to the rolling direction, and subjected to Epstein measurement.

It is believed here that there was almost no strain in a sample subjected to electric discharge machining, that is, there was no machining affected zone. Hence, it is considered that if, in the model illustrated in FIG. 5, the iron loss of a sample subjected to electric discharge machining is used as the iron loss in the non-machining-affected zone of a shear-cut sample, then the iron loss of the shear-cut sample can be expressed by:

iron loss ($B_0$) of the shear-cut sample=[iron loss ($B_1$) of the sample subjected to electric discharge machining]*[a width ratio of the non-machining-affected zone]+[iron loss ($B_2$) of the machining affected zone of the shear-cut sample]*[a width ratio of the machining affected zone]   (1)

Where "a width ratio of the machining affected zone" refers to the ratio of a total machining affected width to the sample width of the shear-cut sample, and "a width ratio of the non-machining-affected zone" refers to the ratio of a total non-machining-affected width to the sample width of the shear-cut sample.

From the results of Experiment 1, the machining affected width of the shear-cut sample was set to 1.5 mm, and boundary values between the machining affected zone and the non-machining-affected zone were set.

In addition, FIG. 7 illustrates the relationship between $B_0$ and $B_1$, $B_2$ in the low-magnetic flux density region (Region A) in which mean magnetic flux density $B_0$ ranges from 0 T to 0.3 T.

As illustrated in FIG. 7, each sample used in this case has a sheet thickness of 0.5 mm, and the upper limit $B_a$ for the mean magnetic flux density in Region A is set to 0.3 T based on the results of Experiment 1, assuming that magnetic flux density of the non-machining-affected zone $B_1$ and magnetic flux density of the machining affected zone $B_2$ are equal ($B_0=B_1=B_2$) up to a point where mean magnetic flux density $B_0$ reaches 0.3 T.

Then, the relationship between $B_0$ and $B_1$, $B_2$ in Region B in which it is easy for the magnetic flux to flow in the non-machining-affected zone in relation to the mean magnetic flux density is set.

From the results of Experiment 1, the upper limit $B_b$ for the mean magnetic flux density $B_0$ in Region B in which it is easy for the magnetic flux to flow in the non-machining-affected zone in relation to mean magnetic flux density $B_0$ is set to 1.45 T.

Additionally, the ratio of increase in magnetic flux density of the non-machining-affected zone $B_1$ to increase in mean magnetic flux density $B_0$, which ratio represents the easiness of flow of magnetic flux in the non-machining-affected zone, can be set to 1.02, and $B_1$ has a value of 0.3 T when it is equal to the lower limit for magnetic flux density $B_0$ (a mean magnetic flux density at the boundary between Region A and Region B=0.3 T). Accordingly, magnetic flux density of the non-machining-affected zone $B_1$ in Region B (in which the mean magnetic flux density ranges between $B_a$ and $B_b$) can be calculated, as illustrated in FIG. 8, by:

$B_1=1.02*B_0-0.006$   (2)

On the other hand, magnetic flux density of the machining affected zone $B_2$ can be calculated by dividing the difference between the total magnetic flux amount and the magnetic flux amount of the non-machining-affected zone by the sectional area of the machining affected zone. That is, as illustrated in FIG. 8, it can be calculated by:

$B_2=(B_0-B_1)*$[a width ratio of the non-machining-affected zone])/[a width ratio of the machining affected zone]   (3)

From equations (2) and (3), if mean magnetic flux density $B_0=B_b$ (1.45 T), then $B_1$ and $B_2$ are calculated to be equal to 1.47 T and 1.40 T, respectively. In equation (3), the width ratios of the machining affected zone and of the non-machining-affected zone are the width ratios of the machining affected zone and of the non-machining-affected zone of the shear-cut sample. In this case, the machining affected width of the shear-cut sample can be set to 1.5 mm from the results of Experiment 1, and a test piece formed by combining such samples contains a total of six machining affected zones, as illustrated in FIG. 6B. Therefore, the width ratio of the machining affected zone of the shear-cut sample can be calculated as 1.5 mm*6 locations/30 mm, and the width ratio of the non-machining-affected zone as (30 mm−1.5 mm*6 locations)/30 mm.

Then, the relationship between $B_0$ and $B_1$, $B_2$ in Region C in which it is difficult for the magnetic flux to flow in the non-machining-affected zone in relation to the mean magnetic flux density is set.

The ratio of increase in magnetic flux density of the non-machining-affected zone $B_1$ to increase in mean magnetic flux density $B_0$, which ratio represents the easiness of flow of magnetic flux in the non-machining-affected zone, can be set to 0.93, and $B_1$ has a value of 1.47 T according to equation (2) when it is equal to the lower limit for the mean magnetic flux density in Reason C (a mean magnetic flux density at the boundary between Region B and Region C=1.45 T). Accordingly, the magnetic flux density in the non-machining-affected zone between $B_b$ and $B_c$ (in Region C) can be calculated, as illustrated in FIG. 8, by:

$B_1=0.93*B_0+0.1215$   (4)

On the other hand, magnetic flux density of the machining affected zone $B_2$ can be calculated by dividing the difference between the total magnetic flux amount and the magnetic flux amount of the non-machining-affected zone by the sectional area of the machining affected zone; that is, it can be calculated by equation (3).

From equations (3) and (4), mean magnetic flux density $B_0$ when $B_1=B_2$, in other words, the upper limit, $B_c$, for the mean magnetic flux density in Region C in which it is difficult for the magnetic flux to flow in the non-machining-affected zone in relation to the mean magnetic flux density, is calculated to be equal to 1.73 T.

Further, the high-magnetic flux density region (Region D) in which the mean magnetic flux density exceeds 1.73 T is set as a region in which magnetic flux density of the non-machining-affected zone $B_1$ and magnetic flux density of the machining affected zone $B_2$ increase at the same rate as mean magnetic flux density $B_0$ increases so that the relation $B_0=B_1=B_2$ is satisfied.

Since the relationship between $B_0$ and $B_1$, $B_2$ for each region is specified as above, the iron loss in the machining affected zone of the shear-cut sample is derived using equation (1) on the basis of these relations. FIGS. 9A and 9B illustrate the magnetic property (iron loss) measurement results for samples subjected to electric discharge machining and for shear-cut samples, respectively.

For example, if mean magnetic flux density $B_0$ is 1.0 T, then from equation (2), magnetic flux density of the non-machining-affected zone $B_1$ is 1.014 T. Thus, assuming that the mean magnetic flux density $B_0$ is 1.0 T, the iron loss value for the magnetic flux density of 1.014 T in FIG. 9A may be used as the iron loss ($B_1$) of the sample subjected to electric discharge machining in equation (1).

Then, using these values and equation (1), the iron loss in the machining affected zone of the shear-cut sample is derived.

If mean magnetic flux density $B_0$ is 1.0 T, then from equations (2) and (3), magnetic flux density of the machining affected zone $B_2$ is equal to 0.967 T. Therefore, the iron loss in the machining affected zone derived in this case represents the iron loss in the machining affected zone with $B_2=0.967$ T.

As illustrated in FIGS. 9A and 9B, the iron loss of the entire shear-cut sample was 1.189 W/kg for magnetic flux density of 1.0 T, and the iron loss of the entire sample subjected to electric discharge machining was 0.968 W/kg for magnetic flux density of 1.014 T.

From Experiment 1, since the machining affected width of this sample can be set to 1.5 mm per location, the width ratio of the machining affected zone in the shear-cut sample can be calculated as 1.5 mm*6 locations/30 mm (=9 mm/30 mm) and the width ratio of the non-machining-affected zone as (30 mm−1.5 mm*6 places)/30 mm (=21 mm/30 mm).

When the relationship between $B_0$ and $B_1$, $B_2$, as well as the iron loss values and the width ratios are substituted into equation (1), the following relation is obtained:

1.189 W/kg ($B_0$=1.0 T)=0.968 W/kg ($B_1$=1.014 T)*21 mm/30 mm+iron loss in the machining affected zone of the shear-cut sample ($B_2$=0.967 T)*9 mm/30 mm As a result, the iron loss in the machining affected zone of the shear-cut sample at $B_2$=0.967 T is derived as 1.71 W/kg.

In this way, the iron loss in the machining affected zone in relation to the magnetic flux density of the machining affected zone $B_2$ was derived. FIG. 10 illustrates the relationship between the derived iron loss and the magnetic flux density of the machining affected zone. In this case, the magnetic flux density corresponds to $B_2$.

Measurement was separately made of the iron loss of a steel sheet of the same material as the above-described samples upon application of a uniaxial compressive stress of 100 MPa in the rolling direction (this iron loss will also be referred to as "uniaxial compressive stress iron loss"). The measurement results are also plotted in FIG. 10.

It can be seen from FIG. 10 that the derived iron loss in the machining affected zone substantially agrees with the uniaxial compressive stress iron loss at 100 MPa.

Moreover, for the uniaxial compressive stress iron loss, the increase in iron loss tends to reach almost saturation even upon a stress of 100 MPa or more being applied to the steel sheet. Therefore, the iron loss in the machining affected zone can be substituted by a uniaxial compressive stress iron loss as measured upon a uniaxial compressive stress of 100 MPa or more being applied to a steel sheet of the same material as the steel sheet to be predicted.

Experiment 3

The 0.5-mm thick non-oriented electrical steel sheet used in Experiment 2 was subjected to shearing by shear cutting (shearing) to obtain a sample of 5 mm wide and 280 mm long.

Thereafter, as illustrated in FIG. 11, six sheets of such samples were combined into a test piece having a total width of 30 mm. In this way, four test pieces were prepared with their longitudinal direction parallel to the rolling direction, and subjected to Epstein measurement.

A comparison was made between the measured value of iron loss of a sample thus sheared to a width of 5 mm and the predicted value estimated using the iron loss of the sample subjected to electric discharge machining and the iron loss of the machining affected zone determined in Experiment 2.

The following specifically describes how the iron loss of the sample sheared to a width of 5 mm was estimated.

First, the relationship between $B_0$ and $B_1$, $B_2$ in FIG. 12 will be described.

In this experiment, the same steel sheet (sheet thickness=0.5 mm) as in Experiment 1 was used. Therefore, for the sample sheared to a width of 5 mm used in this experiment, the easiness of flow of magnetic flux can also be considered the same for the non-machining-affected zone and the machining affected zone ($B_0=B_1=B_2$) in the low-magnetic flux density region (Region A) in which mean magnetic flux density $B_0$ ranges from 0 T to 0.3 T.

Then, the relationship between $B_0$ and $B_1$, $B_2$ for Region B in which it is easy for the magnetic flux to flow in the non-machining-affected zone in relation to the mean magnetic flux density is set.

As is the case with Experiment 2, from the results of Experiment 1, the upper limit $B_b$ for the mean magnetic flux density $B_0$ in Region B in which it is easy for the magnetic flux to flow in the non-machining-affected zone in relation to the mean magnetic flux density is set to 1.45 T.

Additionally, the ratio of increase in magnetic flux density of the non-machining-affected zone $B_1$ to increase in mean magnetic flux density $B_0$, which ratio represents the easiness of flow of magnetic flux in the non-machining-affected zone, can be set to 1.02, and $B_1$ has a value of 0.3 T when it is equal to the lower limit for the mean magnetic flux density in Region B (a mean magnetic flux density at the boundary between Region A and Region B=0.3 T). Accordingly, magnetic flux density of the non-machining-affected zone $B_1$ in Region B (in which the mean magnetic flux density ranges between $B_a$ and $B_b$) can be calculated by:

$$B_1 = 1.02 * B_0 - 0.006 \quad (2)$$

On the other hand, magnetic flux density of the machining affected zone $B_2$ can be calculated by dividing the difference between the total magnetic flux amount and the magnetic flux amount of the non-machining-affected zone by the sectional area of the machining affected zone; that is, it can be calculated by:

$$B_2 = (B_0 - B_1) * [\text{a width ratio of the non-machining-affected zone}] / [\text{a width ratio of the machining affected zone}] \quad (3)$$

From equations (2) and (3), if mean magnetic flux density $B_0 = B_b$ (1.45 T), then $B_1$ and $B_2$ are calculated to be equal to 1.47 T and 1.44 T, respectively.

In equation (3), the width ratios of the machining affected zone and of the non-machining-affected zone are the width ratios of the machining affected zone and of the nonmachining-affected zone of the sample shear-cut to a width of 5 mm. In this case, the machining affected width of the sample used in the experiment having a width of 5 mm after subjection to shearing can be set to 1.5 mm from the results of Experiment 1, and a test piece formed by combining such samples contains a total of twelve machining affected zones, as illustrated in FIG. 11. Therefore, the width ratio of the machining affected zone in this case can be calculated as 1.5 mm*12 locations/30 mm (=18 mm/30 mm), and the width ratio of the non-machining-affected zone as (30 mm−1.5 mm*12 locations)/30 mm (=12 mm/30 mm).

Then, the relationship between $B_0$ and $B_1$, $B_2$ for Region C in which it is difficult for the magnetic flux to flow in the non-machining-affected zone in relation to the mean magnetic flux density is set.

The ratio of increase in magnetic flux density of the non-machining-affected zone $B_1$ to increase in mean magnetic flux density $B_0$, which ratio represents the easiness of flow of magnetic flux in the non-machining-affected zone, can be set to 0.93, and $B_1$ has a value of 1.47 T according to equation (2) when it is equal to the lower limit for the mean magnetic flux density in Region C (a mean magnetic flux density at the boundary between Region B and Region C=1.45 T). Accordingly, the magnetic flux density of the non-machining-affected zone in Region C (between $B_b$ and $B_c$) can be calculated by:

$$B_1 = 0.93 * B_0 + 0.1215 \quad (4)$$

On the other hand, magnetic flux density of the machining affected zone $B_2$ can be calculated by dividing the difference between the total magnetic flux amount and the magnetic flux amount of the non-machining-affected zone by the sectional area of the machining affected zone; that is, it can be calculated by equation (3).

From equations (3) and (4), mean magnetic flux density $B_0$ when $B_1 = B_2$, in other words, the upper limit $B_c$ for the mean magnetic flux density in Region C in which it is difficult for the magnetic flux to flow in the non-machining-affected zone in relation to the mean magnetic flux density, is calculated to be equal to 1.74 T.

Further, the high-magnetic flux density region (Region D) in which the mean magnetic flux density exceeds 1.74 T is set as a region in which magnetic flux density of the non-machining-affected zone $B_1$ and magnetic flux density of the machining affected zone $B_2$ increase at the same rate as mean magnetic flux density $B_0$ increases so that the relation $B_0 = B_1 = B_2$ is satisfied.

From the relationship between $B_0$ and $B_1$, $B_2$ for each of the above-described regions, and based on the iron loss of the sample subjected to electrical discharge machining and the iron loss of the machining affected zone determined in Experiment 2, the iron loss of the sample shear-cut (sheared) to a width of 5 mm can be calculated using the following equation:

[iron loss ($B_0$) of the sample shear-cut to a width of 5 mm]=[iron loss ($B_1$) of the sample subjected to electric discharge machining determined in Experiment 2]*[a width ratio of the non-machining-affected zone]+[iron loss ($B_2$) of the machining affected zone determined in Experiment 2]*[a width ratio of the machining affected zone] (5)

In equation (5), the width ratios of the machining affected zone and of the non-machining-affected zone are the width ratios of the machining affected zone and of the non-machining-affected zone of the sample shear-cut to a width of 5 mm. Specifically, as described above, the width ratio of the machining affected zone can be calculated as 1.5 mm*12 locations/30 mm (=18 mm/30 mm), and the width ratio of the non-machining-affected zone as (30 mm−1.5 mm*12 locations)/30 mm (=12 mm/30 mm).

FIG. 13 is a plot of the calculation results and measured values of iron loss as a function of mean magnetic flux density $B_0$. It can be seen that the calculation results agree very well with the measured values of iron loss.

From the results of Experiments 1 to 3 above, it was found that the following process enables predicting, with high accuracy, iron loss properties of a non-oriented electrical steel sheet after shearing to a certain width.

(1) To predict the iron loss of a non-oriented electrical steel sheet after shearing with machining strain being introduced by the shearing, iron loss in the non-machining-affected zone in which no machining strain is introduced and iron loss in the machining affected zone in which machining strain is introduced are summed up according to the width ratios of the non-machining-affected zone and of the machining affected zone.

(2) Magnetic flux flows in the non-machining-affected zone and in the machining affected zone are roughly classified into three models (regions) given below according to the mean magnetic flux density.

Region 1: A region in which as mean magnetic flux density $B_0$ increases, magnetic flux density of the non-machining-affected zone $B_1$ and magnetic flux density of the machining affected zone $B_2$ increase at the same rate (corresponding to Region A and Region D in the above experiments).

Region 2: A region in which as mean magnetic flux density $B_0$ increases, magnetic flux density of the non-machining-affected zone $B_1$ increases at a higher rate than magnetic flux density of the machining affected zone $B_2$ (corresponding to Region B in the above experiments).

Region 3: A region in which as mean magnetic flux density $B_0$ increases, magnetic flux density of the machining affected zone $B_2$ increases at a higher rate than magnetic flux density of the non-machining-affected zone $B_1$ (corresponding to Region C in the above experiments).

(3) The iron loss of a sample of the same material as the steel sheet to be predicted with a small degree of influence exerted by the shearing (such as a sample subjected to electric discharge machining with little influence of strain (shearing)) is set as the iron loss in the non-machining-affected zone.

Further, a comparison is made of iron loss of two samples of the same material but with different degrees of influence exerted by cutting work (for example, compare the iron loss of a sample cut by electric discharge machining with that of a sample shear-cut to an arbitrary width, or compare the iron loss of two samples shear-cut to different widths), to thereby derive the iron loss in the machining affected zone.

Therefore, the iron loss in the machining affected zone can be substituted by the uniaxial compressive stress iron loss as measured upon a uniaxial compressive stress of 100 MPa or more being applied to a steel sheet of the same material as the steel sheet to be predicted.

Experiment 4

In the above experiments, the iron loss in the non-machining-affected zone is determined using a sample subjected to electric discharge machining with which strain introduction is minimized. However, electric discharge machining is time-consuming and labor-intensive. It is thus preferable to consider an alternative.

Therefore, to calculate the iron losses of steel sheets sheared to a width of 5 mm according to the above-described process, samples of the same material as used in Experiments 1 to 3 were prepared and shear-cut to 10 mm to 40 mm in width with their longitudinal direction parallel to the rolling direction, the iron loss of each sample was determined and used as the iron loss in the non-machining-affected zone, and the prediction accuracy in each case was investigated by comparing the calculated values with the measured values.

The iron loss in the machining affected zone was derived using a sample having a width of 40 mm and a sample having a width of 10 mm.

In this case, the measured values used for verifying the accuracy of the corresponding calculated values are the measured values of iron loss from Epstein measurements performed on four L-direction test pieces. The L-direction test pieces were formed from samples that were cut out from the material by shear-cutting to a width of 5 mm and a length of 280 mm each, and attached together to have a total width of 30 mm. This is because the samples used for deriving calculation parameters had their longitudinal direction parallel to the rolling direction (L-direction samples). In the case of using C-direction samples for derivation of calculation parameters, measured values for C-direction samples may be used. In the case of using L+C-direction samples for derivation of calculation parameters (by equal amounts in L and C directions), measured values for L+C-direction samples may be used.

The evaluation results are listed in Table 1. In Table 1, "Error in prediction accuracy of iron loss at each excitation magnetic flux density (at 50 Hz) [%]" lists relative values of the calculated values in relation to the measured values of iron loss at the corresponding excitation magnetic flux densities of respective steel sheets sheared to a width of 5 mm.

TABLE 1

| No. | Sample width used in prediction of iron loss in non-machining-affected zone | Error in prediction accuracy of iron loss at each excitation magnetic flux density (at 50 Hz) [%] | | |
|---|---|---|---|---|
| | | 0.5 T | 1.0 T | 1.5 T |
| 1 | 40 | 6 | 6 | 6 |
| 2 | 35 | 5 | 5 | 6 |
| 3 | 30 | 6 | 4 | 4 |
| 4 | 25 | 9 | 9 | 9 |
| 5 | 20 | 12 | 12 | 11 |
| 6 | 15 | 14 | 12 | 11 |
| 7 | 10 | 14 | 14 | 13 |
| 8 | — (In this case, sample subjected to electric discharge machining was used.) | 5 | 6 | 6 |

As presented in Table 1, it was found that if the iron loss of a sample having a width of 30 mm or more is used instead of the iron loss of a sample subjected to electric discharge machining as the iron loss in the non-machining-affected zone, the error in prediction accuracy becomes less significant, enabling accurate prediction of the iron loss of the grain-oriented electrical steel sheet after shearing.

The reason is considered to be that by setting the width to 30 mm or more, the proportion of the entire width accounted for by the strain affected width became very small, resulting in less significant influence being exerted by the machining strain on the iron loss.

Experiment 5

Then we investigated preferred combinations of samples with different degrees of influence exerted by the shearing, that is, samples having different widths after subjection to shearing, for use in derivation of iron loss properties at machining affected zones.

The same material as used in Experiments 1 to 3 were subjected to shearing (shear cutting) to prepare samples having various widths. Then, the iron loss of each sample was measured in the same manner as in Experiments 1 to 3. The iron losses obtained for samples different in width were combined as presented in Table 2, to derive the iron loss in the corresponding machining affected zone according to the process used in Experiments 1 to 3.

From the iron loss in each machining affected zone derived, the iron loss properties of the corresponding sample sheared to a width of 5 mm were predicted and compared with the measured values. As the iron loss in each non-machining-affected zone, the iron loss of the first sample in Table 2 was used.

The evaluation results are listed in Table 2.

TABLE 2

| No. | First sample's width (mm) | Second sample's width (mm) | Error in prediction accuracy of iron loss at each excitation magnetic flux density (at 50 Hz) [%] | | |
|---|---|---|---|---|---|
| | | | 0.5 T | 1.0 T | 1.5 T |
| 1 | 40 | 35 | 14 | 12 | 10 |
| 2 | 40 | 25 | 13 | 10 | 10 |
| 3 | 40 | 15 | 6 | 4 | 4 |
| 4 | 40 | 10 | 5 | 4 | 4 |
| 5 | 30 | 25 | 14 | 13 | 13 |
| 6 | 30 | 15 | 5 | 5 | 5 |
| 7 | 30 | 10 | 5 | 6 | 5 |
| 8 | 20 | 15 | 15 | 15 | 13 |
| 9 | 20 | 10 | 10 | 10 | 10 |
| 10 | 15 | 10 | 12 | 12 | 11 |
| 11 | In this case, a value as conventionally measured according to JIS C 2550 at a width of 30 mm was used as a predicted value. | | 33 | 30 | 28 |

It can be seen from Table 2 that in order to reduce the error in prediction accuracy and to achieve improved accuracy, it is better to calculate the iron loss in the machining affected zone by combining the iron loss of a sample having a width of 30 mm or more and the iron loss of a sample having a width of 15 mm or less.

The reason is considered to be that for each case in which the difference in the degree of influence exerted by machining strain between two samples was made as large as possible, the result was less affected by other factors affecting the iron loss, and consequently the iron loss in the machining affected zone was able to be derived with high accuracy.

Experiment 6

According to the models disclosed herein, the iron loss of a non-oriented electrical steel sheet is predicted by summing up iron loss in the machining affected zone and iron loss in the non-machining-affected zone according to the width ratios of the machining affected zone and of the non-machining-affected zone. It is thus important to accurately determine the machining affected width. Therefore, it is preferable to carry out measurement of elastic stress every time using X-rays or synchrotron radiation, and use the result as the machining affected width.

It is very cumbersome to measure the machining affected width every time, however, and thus we investigated the relationship between machining affected width and prediction accuracy.

In this case, investigations were carries out on samples having different sheet thicknesses from 0.1 mm to 0.5 mm. Used as the iron loss in the machining affected zone was the iron loss of a steel sheet of the same material as the steel sheet to be sheared as measured upon a uniaxial compressive stress of 200 MPa being applied thereto. Also, used as the iron loss in the non-machining-affected zone was the iron loss of a sample sheared (shear-cut) to a width of 30 mm. Then, determination was made of the iron loss (determined by calculation) of each sample sheared to a width of 5 mm, in which case the machining affected width of each sample was set within a range of 0 mm to 5 mm.

The iron losses thus calculated and the measured values were compared. FIGS. 14A to 14D illustrate the relationship between the error in prediction accuracy and the machining affected width set for each sample with a sheet thickness of 0.1 mm to 0.5 mm.

It can be seen from FIGS. 14A-14D that for each case in which the machining affected width was set to be about two to four times the sheet thickness, the error in prediction accuracy was less significant and good prediction accuracy was exhibited. Therefore, from the perspective of improving prediction accuracy, it is preferable to use a value that is two to four times the sheet thickness as the machining affected width.

With any sheet thickness, the error in prediction accuracy was significant for conventional iron loss properties prescribed in JIS C 2550, that is, where deterioration due to strain was not considered (machining affected width=0 mm).

Experiment 7

One of the key points of the disclosure is to set the easiness of flow of magnetic flux in the non-machining-affected zone in the region (Region B) in which it is easy for the magnetic flux to flow in the non-machining-affected zone in relation to mean magnetic flux density $B_0$ described above, and to set the easiness of flow of magnetic flux in the non-machining-affected zone in the region (Region C) in which it is difficult for the magnetic flux to flow in the non-machining-affected zone in relation to the mean magnetic flux density. Therefore, in this experiment, we investigated the allowable range of these set values.

A non-oriented electrical steel sheet of 0.2 mm in sheet thickness was subjected to shear cutting (shearing), and sheared into a sample of 10 mm wide and 280 mm long. Thereafter, three sheets of such samples were combined into a test piece having a total width of 30 mm. In this way, four test pieces were prepared with their longitudinal direction parallel to the rolling direction, and subjected to Epstein measurement.

Similarly, test pieces were prepared by cutting work using electric discharge machining, and subjected to Epstein measurement.

Based on the iron losses thus obtained, the iron losses of individual machining affected zones were set.

In addition, the upper limit $B_a$ for the mean magnetic flux density in Region A was set to 0 T, and the range of mean magnetic flux density for Region B was set to 0 T to 1.45 T. The ratio of increase in magnetic flux density of the non-machining-affected zone $B_1$ to increase in mean magnetic flux density $B_0$, which ratio represents the easiness of flow of magnetic flux in the non-machining-affected zone in Region B, was varied in the range of 1.00 to 1.10.

For Region C in which the mean magnetic flux density ranges from 1.45 T to $B_c$, the ratio of increase in magnetic flux density of the non-machining-affected zone $B_1$ to increase in mean magnetic flux density $B_0$, which ratio represents the easiness of flow of magnetic flux in the non-machining-affected zone, was varied in the range of 0.85 to 1.00. Further, the machining affected width was set to 0.6 mm, which is three times the sheet thickness.

Under such conditions, predictions were made of the iron losses of individual samples sheared to a width of 7.5 mm, and the predicted values were compared with the measured values. The results are listed in Tables 3 and 4.

TABLE 3

| No. | Value set for the ratio* of increase in magnetic flux density of non-machining-affected zone in Region B | Value set for the ratio* of increase in magnetic flux density of non-machining-affected zone in Region C | Error in prediction accuracy of iron loss at each excitation magnetic flux density (at 50 Hz) [%] | | | | | | | | | |
|---|---|---|---|---|---|---|---|---|---|---|---|---|
| | | | 0.15 T | 0.35 T | 0.55 T | 0.75 T | 0.95 T | 1.15 T | 1.35 T | 1.55 T | 1.7 T | 1.85 T |
| 1 | 1.00 | 0.94 | 14 | 14 | 14 | 14 | 14 | 14 | 14 | 11 | 11 | 11 |
| 2 | 1.005 | 0.94 | 9 | 9 | 9 | 8 | 7 | 8 | 8 | 8 | 8 | 8 |
| 3 | 1.01 | 0.94 | 6 | 6 | 6 | 6 | 5 | 6 | 6 | 7 | 7 | 7 |
| 4 | 1.015 | 0.94 | 5 | 4 | 5 | 6 | 6 | 6 | 5 | 6 | 5 | 5 |
| 5 | 1.02 | 0.94 | 6 | 5 | 7 | 5 | 5 | 6 | 6 | 6 | 6 | 6 |
| 6 | 1.025 | 0.94 | 5 | 5 | 4 | 5 | 6 | 5 | 6 | 5 | 6 | 5 |
| 7 | 1.03 | 0.94 | 5 | 5 | 6 | 6 | 5 | 6 | 6 | 5 | 5 | 5 |
| 8 | 1.035 | 0.94 | 8 | 8 | 8 | 7 | 6 | 6 | 8 | 8 | 7 | 7 |
| 9 | 1.04 | 0.94 | 14 | 14 | 14 | 14 | 14 | 14 | 14 | 12 | 11 | 11 |
| 10 | 1.045 | 0.94 | 14 | 15 | 14 | 15 | 14 | 15 | 15 | 11 | 12 | 11 |
| 11 | 1.05 | 0.94 | 16 | 16 | 15 | 15 | 16 | 16 | 16 | 12 | 13 | 12 |
| 12 | 1.06 | 0.94 | 17 | 17 | 18 | 19 | 18 | 17 | 16 | 13 | 13 | 14 |
| 13 | 1.07 | 0.94 | 17 | 17 | 18 | 19 | 18 | 17 | 16 | 13 | 13 | 14 |
| 14 | 1.08 | 0.94 | 18 | 18 | 18 | 18 | 18 | 18 | 18 | 15 | 15 | 15 |
| 15 | 1.09 | 0.94 | 20 | 20 | 20 | 20 | 20 | 20 | 20 | 18 | 18 | 18 |
| 16 | 1.10 | 0.94 | 21 | 21 | 20 | 21 | 20 | 21 | 21 | 18 | 18 | 19 |

*The ratio of increase in magnetic flux density of non-machining-affected zone $B_1$ to increase in mean magnetic flux density $B_0$.

TABLE 4

| | Value set for the ratio* of increase in magnetic flux density of non-machining-affected | Value set for the ratio* of increase in magnetic flux density of non-machining-affected | Error in prediction accuracy of iron loss at each excitation magnetic flux density (at 50 Hz) [%] | | | | | | | | | |
|---|---|---|---|---|---|---|---|---|---|---|---|---|
| No. | zone in Region B | zone in Region C | 0.15 T | 0.35 T | 0.55 T | 0.75 T | 0.95 T | 1.15 T | 1.35 T | 1.55 T | 1.7 T | 1.85 T |
| 1 | 1.015 | 0.85 | 5 | 5 | 5 | 5 | 5 | 5 | 5 | 18 | 20 | 18 |
| 2 | 1.015 | 0.87 | 5 | 4 | 4 | 4 | 5 | 5 | 6 | 18 | 19 | 22 |
| 3 | 1.015 | 0.89 | 5 | 5 | 6 | 7 | 7 | 7 | 7 | 16 | 16 | 16 |
| 4 | 1.015 | 0.91 | 6 | 6 | 6 | 6 | 6 | 6 | 6 | 8 | 8 | 8 |
| 5 | 1.015 | 0.93 | 6 | 5 | 5 | 5 | 5 | 6 | 6 | 6 | 6 | 6 |
| 6 | 1.015 | 0.95 | 5 | 5 | 5 | 5 | 5 | 5 | 5 | 5 | 5 | 5 |
| 7 | 1.015 | 0.97 | 5 | 5 | 6 | 5 | 5 | 5 | 5 | 15 | 16 | 16 |
| 8 | 1.015 | 0.99 | 4 | 4 | 7 | 7 | 5 | 4 | 5 | 18 | 18 | 20 |
| 9 | 1.015 | 1.00 | 5 | 5 | 6 | 5 | 5 | 5 | 5 | 18 | 18 | 18 |

*The ratio of increase in magnetic flux density of non-machining-affected zone $B_1$ to increase in mean magnetic flux density $B_0$.

From Tables 3 and 4, it was revealed that iron loss properties can be predicted with higher accuracy with less significant error in prediction accuracy, if the following conditions are met:
the ratio of increase in magnetic flux density of the non-machining-affected zone $B_1$ to increase in mean magnetic flux density $B_0$, which ratio represents the easiness of flow of magnetic flux in the non-machining-affected zone in Region B, is set to 1.02±0.015; and
the ratio of increase in magnetic flux density of the non-machining-affected zone $B_1$ to increase in mean magnetic flux density $B_0$, which ratio represents the easiness of flow of magnetic flux in the non-machining-affected zone in Region C, is set to 0.93±0.02.

Experiment 8

Then, accuracy investigation was made on the process of setting the region (Region A) in which the magnetic flux flows with equal ease in the non-machining-affected zone and in the machining affected zone in the low-magnetic flux density region.
Non-oriented electrical steel sheets, steel types A to I, of 0.23 mm to 0.55 mm in sheet thickness with different compositions, were respectively shear-cut (sheared) 7.5 mm in width, and sheared into samples of 7.5 mm wide and 280 mm long. Thereafter, four sheets of such samples were combined into a test piece having a total width of 30 mm. In this way, four test pieces were prepared with their longitudinal direction parallel to the rolling direction, and subjected to Epstein measurement.
Similarly, test pieces were prepared by cutting work using electric discharge machining, and subjected to Epstein measurement.

Based on the iron losses thus measured, the iron losses were respectively set for the machining affected zones of the steel sheets of steel types A to I.
Then, we investigated the accuracy of prediction of various values that were set for $B_a$, which is the upper limit for the mean magnetic flux density in Region A, in relation to $B_{as}$, which is calculated, as illustrated in FIG. 4, by:

$$B_{as}=0 \text{ (for } t \leq 0.25 \text{ mm)},$$

$$B_{as}=1.2*t-0.3 \text{ (for } 0.25 \text{ mm} < t \leq 0.50 \text{ mm)}, \text{ and}$$

$$B_{as}=0.3 \text{ (for } 0.5 \text{ mm} < t) \tag{6}$$

In this case, $B_b$, which is the upper limit for the mean magnetic flux density in Region B, was set to 1.45 T. In addition, the ratio of increase in magnetic flux density of the non-machining-affected zone $B_1$ to increase in mean magnetic flux density $B_0$, which ratio represents the easiness of flow of magnetic flux in the non-machining-affected zone in Region B in which the mean magnetic flux density ranges from $B_a$ to 1.45 T, was set to 1.03.
Further, the ratio of increase in magnetic flux density of the non-machining-affected zone $B_1$ to increase in mean magnetic flux density $B_0$, which ratio represents the easiness of flow of magnetic flux in the non-machining-affected zone in Region C in which the mean magnetic flux density ranges from 1.45 T to $B_c$ T, was set to 0.95.
In each case, the machining affected width was set to 2.5 times the sheet thickness.
Under such conditions, predictions were made of the iron losses of individual samples sheared to a width of 10 mm, and the predicted values were compared with the measured values. The results are listed in Tables 5 to 7.

TABLE 5

| Steel type | Sheet thickness (mm) | $B_{as}$ (T) | $B_a$ (T) | Error in prediction accuracy of iron loss at each excitation magnetic flux density (at 50 Hz) [%] | | | | | | |
|---|---|---|---|---|---|---|---|---|---|---|
| | | | | 0.1 T | 0.2 T | 0.3 T | 0.4 T | 0.5 T | 0.6 T | 0.7 T |
| A | 0.23 | 0 | 0 | 5 | 5 | 5 | 6 | 4 | 5 | 6 |
| | | | 0.05 | 5 | 6 | 5 | 4 | 4 | 5 | 4 |
| | | | 0.1 | 6 | 6 | 5 | 5 | 5 | 5 | 5 |
| | | | 0.15 | 6 | 6 | 6 | 6 | 6 | 6 | 6 |
| | | | 0.2 | 8 | 8 | 7 | 8 | 9 | 8 | 8 |
| | | | 0.25 | 14 | 15 | 15 | 15 | 14 | 14 | 15 |
| | | | 0.3 | 14 | 15 | 14 | 13 | 14 | 15 | 15 |
| | | | 0.4 | 16 | 16 | 16 | 16 | 16 | 16 | 16 |

TABLE 5-continued

| Steel type | Sheet thickness (mm) | $B_{as}$ (T) | $B_a$ (T) | Error in prediction accuracy of iron loss at each excitation magnetic flux density (at 50 Hz) [%] | | | | | | |
|---|---|---|---|---|---|---|---|---|---|---|
| | | | | 0.1 T | 0.2 T | 0.3 T | 0.4 T | 0.5 T | 0.6 T | 0.7 T |
| B | 0.23 | 0 | 0 | 7 | 7 | 7 | 7 | 7 | 7 | 7 |
| | | | 0.05 | 5 | 6 | 6 | 4 | 5 | 6 | 6 |
| | | | 0.1 | 6 | 6 | 5 | 5 | 5 | 5 | 5 |
| | | | 0.15 | 5 | 5 | 6 | 6 | 5 | 6 | 6 |
| | | | 0.2 | 7 | 8 | 7 | 8 | 9 | 7 | 8 |
| | | | 0.25 | 7 | 8 | 8 | 8 | 8 | 8 | 8 |
| | | | 0.3 | 15 | 14 | 14 | 14 | 15 | 14 | 13 |
| | | | 0.4 | 15 | 15 | 15 | 16 | 16 | 16 | 16 |
| C | 0.23 | 0 | 0 | 8 | 7 | 7 | 7 | 7 | 7 | 7 |
| | | | 0.05 | 6 | 6 | 6 | 6 | 6 | 6 | 6 |
| | | | 0.1 | 5 | 5 | 4 | 4 | 3 | 5 | 4 |
| | | | 0.15 | 4 | 5 | 6 | 5 | 5 | 5 | 6 |
| | | | 0.2 | 6 | 6 | 6 | 6 | 7 | 4 | 5 |
| | | | 0.25 | 6 | 6 | 7 | 7 | 7 | 7 | 7 |
| | | | 0.3 | 8 | 8 | 8 | 9 | 8 | 7 | 10 |
| | | | 0.4 | 16 | 16 | 16 | 16 | 16 | 16 | 16 |

TABLE 6

| Steel type | Sheet thickness (mm) | $B_{as}$ (T) | $B_a$ (T) | Error in prediction accuracy of iron loss at each excitation magnetic flux density (at 50 Hz) [%] | | | | | | |
|---|---|---|---|---|---|---|---|---|---|---|
| | | | | 0.1 T | 0.2 T | 0.3 T | 0.4 T | 0.5 T | 0.6 T | 0.7 T |
| D | 0.35 | 0.11 | 0 | 7 | 7 | 7 | 7 | 7 | 7 | 7 |
| | | | 0.05 | 6 | 6 | 5 | 5 | 5 | 5 | 5 |
| | | | 0.11 | 4 | 5 | 5 | 5 | 4 | 4 | 5 |
| | | | 0.15 | 5 | 5 | 6 | 6 | 6 | 6 | 6 |
| | | | 0.25 | 7 | 7 | 7 | 8 | 9 | 9 | 8 |
| | | | 0.35 | 12 | 14 | 13 | 13 | 12 | 12 | 14 |
| | | | 0.4 | 14 | 13 | 14 | 14 | 14 | 15 | 16 |
| | | | 0.45 | 16 | 17 | 17 | 16 | 16 | 17 | 16 |
| E | 0.35 | 0.11 | 0 | 8 | 8 | 9 | 7 | 8 | 7 | 9 |
| | | | 0.05 | 7 | 7 | 8 | 8 | 7 | 6 | 6 |
| | | | 0.11 | 6 | 5 | 6 | 7 | 6 | 6 | 6 |
| | | | 0.15 | 5 | 5 | 6 | 6 | 5 | 6 | 6 |
| | | | 0.25 | 6 | 6 | 7 | 7 | 7 | 7 | 6 |
| | | | 0.32 | 8 | 8 | 8 | 8 | 8 | 8 | 8 |
| | | | 0.4 | 15 | 14 | 14 | 13 | 13 | 12 | 14 |
| | | | 0.45 | 15 | 14 | 13 | 14 | 14 | 15 | 16 |
| F | 0.35 | 0.11 | 0 | 9 | 9 | 10 | 9 | 10 | 9 | 9 |
| | | | 0.05 | 8 | 8 | 8 | 7 | 7 | 7 | 7 |
| | | | 0.11 | 7 | 6 | 6 | 7 | 6 | 6 | 6 |
| | | | 0.15 | 5 | 5 | 5 | 5 | 5 | 5 | 6 |
| | | | 0.25 | 5 | 5 | 5 | 4 | 5 | 4 | 5 |
| | | | 0.32 | 6 | 6 | 6 | 6 | 6 | 6 | 6 |
| | | | 0.4 | 7 | 8 | 8 | 7 | 8 | 7 | 10 |
| | | | 0.45 | 18 | 17 | 16 | 18 | 16 | 16 | 16 |

TABLE 7

| Steel type | Sheet thickness (mm) | $B_{as}$ (T) | $B_a$ (T) | Error in prediction accuracy of iron loss at each excitation magnetic flux density (at 50 Hz) [%] | | | | | | |
|---|---|---|---|---|---|---|---|---|---|---|
| | | | | 0.1 T | 0.2 T | 0.3 T | 0.4 T | 0.5 T | 0.6 T | 0.7 T |
| G | 0.55 | 0.3 | 0 | 20 | 21 | 22 | 20 | 19 | 20 | 20 |
| | | | 0.05 | 15 | 16 | 15 | 14 | 16 | 17 | 16 |
| | | | 0.1 | 9 | 9 | 8 | 8 | 9 | 9 | 9 |
| | | | 0.15 | 6 | 7 | 6 | 6 | 7 | 7 | 7 |
| | | | 0.3 | 4 | 4 | 4 | 5 | 5 | 5 | 6 |
| | | | 0.4 | 6 | 5 | 5 | 6 | 6 | 5 | 5 |
| | | | 0.5 | 7 | 7 | 7 | 8 | 8 | 9 | 8 |
| | | | 0.6 | 15 | 14 | 15 | 15 | 15 | 14 | 15 |
| H | 0.55 | 0.3 | 0 | 14 | 18 | 16 | 17 | 18 | 15 | 14 |
| | | | 0.05 | 8 | 9 | 9 | 8 | 8 | 9 | 9 |
| | | | 0.1 | 7 | 6 | 7 | 7 | 7 | 6 | 6 |
| | | | 0.15 | 4 | 4 | 4 | 5 | 4 | 4 | 4 |
| | | | 0.3 | 6 | 6 | 7 | 7 | 7 | 7 | 6 |

TABLE 7-continued

| Steel type | Sheet thickness (mm) | $B_{as}$ (T) | $B_a$ (T) | Error in prediction accuracy of iron loss at each excitation magnetic flux density (at 50 Hz) [%] | | | | | | |
|---|---|---|---|---|---|---|---|---|---|---|
| | | | | 0.1 T | 0.2 T | 0.3 T | 0.4 T | 0.5 T | 0.6 T | 0.7 T |
| I | 0.55 | 0.3 | 0.4 | 8 | 8 | 8 | 8 | 8 | 8 | 8 |
| | | | 0.5 | 10 | 9 | 9 | 9 | 10 | 9 | 9 |
| | | | 0.6 | 15 | 14 | 13 | 14 | 14 | 15 | 16 |
| | | | 0 | 18 | 17 | 16 | 15 | 15 | 16 | 17 |
| | | | 0.05 | 17 | 17 | 15 | 15 | 14 | 15 | 15 |
| | | | 0.1 | 10 | 9 | 9 | 8 | 9 | 9 | 9 |
| | | | 0.15 | 7 | 6 | 7 | 6 | 7 | 7 | 7 |
| | | | 0.3 | 5 | 5 | 5 | 5 | 5 | 5 | 5 |
| | | | 0.4 | 4 | 5 | 4 | 5 | 5 | 4 | 4 |
| | | | 0.5 | 7 | 7 | 7 | 8 | 8 | 8 | 8 |
| | | | 0.6 | 9 | 9 | 9 | 9 | 8 | 9 | 8 |

From Tables 5 to 7, it was revealed that iron loss properties can be predicted with high accuracy regardless of the composition when the following conditions are met: $B_a=0$ T to 0.2 T for sheet thickness equal to or less than 0.25 mm (steel types A to C) and $B_a=B_{as}\pm0.2$ T ($\geq 0$ T) for sheet thickness greater than 0.25 mm (steel types D to I).

The reason why the preferred range varied for different samples is considered to be that the reference magnetic flux density for $B_a$ slightly changes depending on conditions such as the composition of the sample.

However, it was found that the variation in reference magnetic flux density can be sufficiently canceled by setting in the above ranges.

Experiment 9

Next, investigation was made on the preferred setting range for the upper limit $B_b$ for the mean magnetic flux density in Region B in which it is easy for the magnetic flux to flow in the non-machining-affected zone in relation to the mean magnetic flux density.

Non-oriented electrical steel sheets, steel types J to N, of 0.35 mm in sheet thickness with different compositions, were respectively shear-cut (sheared) 5.0 mm in width, and sheared into samples of 5 mm wide and 280 mm long. Thereafter, six sheets of such samples were combined into a test piece having a total width of 30 mm. In this way, four test pieces were prepared with their longitudinal direction parallel to the rolling direction, and subjected to Epstein measurement.

Similarly, test pieces were prepared by cutting work using electric discharge machining, and subjected to Epstein measurement.

The iron loss in each machining affected zone was set on the basis of the iron loss of the corresponding sample determined as described above.

Then, we investigated the prediction accuracy by varying values of $B_b$, which is the upper limit for the mean magnetic flux density in Region B.

In this case, $B_a$, which is the upper limit for the mean magnetic flux density in Region A, was set to 0.15 T. In addition, the ratio of increase in magnetic flux density of the non-machining-affected zone $B_1$ to increase in mean magnetic flux density $B_0$, which ratio represents the easiness of flow of magnetic flux in the non-machining-affected zone in Region B in which the mean magnetic flux density ranges from 0.15 T to $B_b$ T, was set to 1.015. Further, in Region C in which the mean magnetic flux density ranges from $B_b$ T to $B_c$ T, the ratio of increase in magnetic flux density of the non-machining-affected zone $B_1$ to increase in mean magnetic flux density $B_0$, which ratio represents the easiness of flow of magnetic flux in the non-machining-affected zone in Region C, was set to 0.93. In each case, the machining affected width was set to 3.5 times the sheet thickness.

Under such conditions, predictions were made of the iron losses of individual samples sheared to a width of 10 mm, and the predicted values were compared with the measured values. The results are listed in Table 8.

TABLE 8

| Steel type | Sheet thickness (mm) | $B_b$ (T) | Error in prediction accuracy of iron loss at each excitation magnetic flux density (at 50 Hz) [%] | | | | | | |
|---|---|---|---|---|---|---|---|---|---|
| | | | 1.2 T | 1.3 T | 1.4 T | 1.5 T | 1.6 T | 1.7 T | 1.8 T |
| J | 0.35 | 1.2 | 18 | 19 | 18 | 20 | 22 | 19 | 19 |
| | | 1.25 | 8 | 16 | 17 | 16 | 16 | 16 | 16 |
| | | 1.3 | 7 | 5 | 9 | 8 | 8 | 7 | 8 |
| | | 1.35 | 7 | 6 | 7 | 6 | 6 | 6 | 6 |
| | | 1.45 | 5 | 5 | 5 | 4 | 4 | 5 | 5 |
| | | 1.55 | 7 | 7 | 7 | 8 | 6 | 6 | 6 |
| | | 1.6 | 5 | 5 | 5 | 5 | 7 | 7 | 7 |
| | | 1.65 | 4 | 4 | 4 | 5 | 9 | 15 | 15 |
| | | 1.7 | 5 | 5 | 6 | 8 | 9 | 18 | 19 |
| K | 0.35 | 1.2 | 15 | 15 | 14 | 13 | 14 | 15 | 15 |
| | | 1.25 | 9 | 9 | 9 | 9 | 9 | 9 | 9 |
| | | 1.3 | 7 | 7 | 7 | 7 | 8 | 7 | 7 |
| | | 1.35 | 5 | 5 | 5 | 5 | 6 | 6 | 6 |
| | | 1.45 | 5 | 5 | 6 | 6 | 5 | 6 | 6 |
| | | 1.55 | 8 | 7 | 7 | 7 | 8 | 7 | 8 |
| | | 1.6 | 9 | 10 | 9 | 10 | 9 | 9 | 9 |
| | | 1.65 | 4 | 4 | 4 | 5 | 9 | 18 | 19 |
| | | 1.7 | 5 | 5 | 6 | 8 | 9 | 20 | 21 |
| L | 0.35 | 1.2 | 21 | 22 | 22 | 21 | 20 | 22 | 22 |
| | | 1.25 | 8 | 15 | 14 | 16 | 15 | 15 | 16 |
| | | 1.3 | 6 | 9 | 8 | 9 | 9 | 9 | 9 |
| | | 1.35 | 5 | 5 | 6 | 6 | 7 | 6 | 6 |
| | | 1.45 | 4 | 5 | 5 | 5 | 6 | 5 | 6 |
| | | 1.55 | 5 | 6 | 5 | 6 | 7 | 4 | 5 |
| | | 1.6 | 7 | 6 | 7 | 6 | 7 | 6 | 6 |
| | | 1.65 | 5 | 5 | 5 | 6 | 8 | 7 | 10 |
| | | 1.7 | 6 | 6 | 6 | 7 | 8 | 15 | 16 |
| M | 0.35 | 1.2 | 9 | 9 | 9 | 10 | 8 | 9 | 9 |
| | | 1.25 | 8 | 8 | 8 | 9 | 8 | 8 | 8 |
| | | 1.3 | 4 | 5 | 6 | 5 | 5 | 6 | 6 |
| | | 1.35 | 6 | 6 | 6 | 5 | 6 | 5 | 5 |
| | | 1.45 | 6 | 7 | 8 | 7 | 7 | 7 | 7 |
| | | 1.55 | 8 | 8 | 9 | 9 | 9 | 7 | 8 |
| | | 1.6 | 5 | 6 | 5 | 6 | 10 | 10 | 9 |
| | | 1.65 | 9 | 9 | 8 | 7 | 15 | 14 | 13 |
| | | 1.7 | 6 | 7 | 8 | 8 | 18 | 19 | 20 |
| N | 0.35 | 1.2 | 24 | 25 | 26 | 25 | 22 | 21 | 22 |
| | | 1.25 | 8 | 18 | 19 | 19 | 20 | 20 | 20 |
| | | 1.3 | 8 | 8 | 8 | 9 | 10 | 10 | 9 |
| | | 1.35 | 6 | 6 | 5 | 7 | 7 | 6 | 7 |
| | | 1.45 | 5 | 5 | 4 | 5 | 5 | 5 | 4 |
| | | 1.55 | 4 | 4 | 4 | 4 | 4 | 4 | 4 |

TABLE 8-continued

| Steel type | Sheet thickness (mm) | $B_b$ (T) | Error in prediction accuracy of iron loss at each excitation magnetic flux density (at 50 Hz) [%] | | | | | | |
|---|---|---|---|---|---|---|---|---|---|
| | | | 1.2 T | 1.3 T | 1.4 T | 1.5 T | 1.6 T | 1.7 T | 1.8 T |
| | | 1.6 | 5 | 6 | 6 | 6 | 5 | 5 | 5 |
| | | 1.65 | 6 | 6 | 7 | 7 | 6 | 7 | 7 |
| | | 1.7 | 9 | 9 | 10 | 9 | 10 | 9 | 9 |

From Table 8, it was revealed that although the preferred value for $B_b$ at which the error in prediction accuracy will be less significant slightly varies depending on the samples, it is possible to accurately predict the iron losses of all the samples regardless of the compositions if $B_b$ is set in the range of 1.45±0.15 T.

Based on the above experimental results, it was discovered that it is important to appreciate the following points in order to predict the iron loss of a non-oriented electrical steel sheet after machining more easily and with higher accuracy.

Substitute the iron loss in a non-machining-affected zone by the iron loss of a sample sheared to a width of 30 mm or more.

To derive the iron loss in a machining affected zone in which machining strain is introduced, combine the iron loss of a sample sheared to a width of 15 mm or less with the iron loss of a sample sheared to a width of 30 mm or more.

Set a machining affected width in the sample (steel sheet) to be predicted that is two to four times the sheet thickness.

Set the easiness of flow of magnetic flux in the non-machining-affected zone in Region B and C within a predetermined range as described above.

Set the boundary values at which the flow of magnetic flux changes (specifically, $B_a$ as the upper limit for the mean magnetic flux density in Region A and $B_b$ as the upper limit for the mean magnetic flux density in Region B) within predetermined ranges.

Based on these findings, we conducted further investigation which eventually led to the present disclosure.

Specifically, the primary features of the disclosure can be summarized as follows:

1. A method for predicting iron loss of a non-oriented electrical steel sheet after shearing to a certain width so that the non-oriented electrical steel sheet comprises a non-machining-affected zone in which no machining strain is introduced and a machining affected zone in which machining strain is introduced, the method comprising:

estimating the iron loss of the non-oriented electrical steel sheet after shearing $Wt(B_0)$ based on iron loss in the non-machining-affected zone $Wn(B_1)$ and iron loss in the machining affected zone $Wi(B_2)$ according to the following equation:

$$Wt(B_0)=Wn(B_1)*[\text{a width ratio of the non-machining-affected zone}]+Wi(B_2)*[\text{a width ratio of the machining affected zone}]$$

where $B_0$, $B_1$, and $B_2$ respectively denote a mean magnetic flux density of the non-oriented electrical steel sheet after shearing, a magnetic flux density of the non-machining-affected zone, and a magnetic flux density of the machining affected zone, upon excitation of the non-oriented electrical steel sheet after shearing, and where the width ratio of the non-machining-affected zone and the width ratio of the machining affected zone are a ratio of a total width of the non-machining-affected zone, and alternatively a ratio of a total width of the machining affected zone, to an entire width of the non-oriented electrical steel sheet after shearing, respectively.

2. The method for predicting iron loss of a non-oriented electrical steel sheet after shearing according to 1., wherein a relationship between the mean magnetic flux density $B_0$ and the magnetic flux densities $B_1$, $B_2$ is set for each of the regions defined as Regions 1 to 3 below according to a value of the mean magnetic flux density $B_0$, and based on the setting, a value of the magnetic flux density $B_1$ and a value of the magnetic flux density $B_2$ for each region are derived:

Region 1 is a region in which as the mean magnetic flux density $B_0$ increases, the magnetic flux density of the non-machining-affected zone $B_1$ and the magnetic flux density of the machining affected zone $B_2$ increase at the same rate;

Region 2 is a region in which as the mean magnetic flux density $B_0$ increases, the magnetic flux density of the non-machining-affected zone $B_1$ increases at a higher rate than the magnetic flux density of the machining affected zone $B_2$; and Region 3 is a region in which as the mean magnetic flux density $B_0$ increases, the magnetic flux density of the machining affected zone $B_2$ increases at a higher rate than the magnetic flux density of the non-machining-affected zone $B_1$.

3. The method for predicting iron loss of a non-oriented electrical steel sheet after shearing according to 1. or 2., wherein as the iron loss $Wn(B_1)$ of the non-machining-affected zone, iron loss of a sample having a width of 30 mm or more which is sheared from a steel sheet of the same material as the non-oriented electrical steel sheet is used.

4. The method for predicting iron loss of a non-oriented electrical steel sheet after shearing according to any one of 1. to 3., wherein the iron loss $Wi(B_2)$ of the machining affected zone is set based on iron loss of a sample having a width of 15 mm or less and iron loss of a sample having a width of 30 mm or more, both sheared from a steel sheet of the same material as the non-oriented electrical steel sheet by deriving the iron loss $Wi(B_2)$ by the following equation:

$$Wi(B_2)=(W_{s1}(B_0)-W_{s2}(B_1)*[\text{a width ratio of the non-machining-affected zone of the sample having a width of 30 mm or more}])/[\text{a width ratio of the machining affected zone of the sample having a width of 15 mm or less}]$$

where $W_{s1}(B_0)$ denotes the iron loss of the sample having a width of 15 mm or less and $W_{s2}(B_1)$ denotes the iron loss of the sample having a width of 30 mm or more, and where the width ratio of the non-machining-affected zone in the sample having a width of 30 mm or more is a ratio of a total width of the non-machining-affected zone to an entire width of the sample, and the width ratio of the machining affected zone of the sample having a width of 15 mm or less is a ratio of a total width of the machining affected zone to the entire width of the sample.

5. The method for predicting iron loss of a non-oriented electrical steel sheet after shearing according to any of 1. to 3., wherein as the iron loss $Wi(B_2)$ of the machining affected zone, iron loss as measured upon a uniaxial compressive stress of 100 MPa or more being applied to the non-oriented electrical steel sheet is used.

6. The method for predicting iron loss of a non-oriented electrical steel sheet after shearing according to any one of 1. to 5., wherein the total width of the machining affected zone of the non-oriented electrical steel sheet after shearing is set to be two to four times a sheet thickness t of the non-oriented electrical steel sheet after shearing.

7. The method for predicting iron loss of a non-oriented electrical steel sheet after shearing according to any one of 2. to 6., wherein a range in which the mean magnetic flux density $B_0$ ranges from 0 T to $B_a$ T is set as the Region 1, and $B_{as}$ is derived as a reference value for $B_a$ according to a sheet thickness t of the non-oriented electrical steel sheet after shearing from the following equations, and $B_a$ is selected in a range of the reference value $B_{as}\pm 0.2$ T (where $B_a$ 0 T):

$B_{as}=0$ (for $t\leq 0.25$ mm), $B_{as}=1.2*t-0.3$ (for 0.25 mm$<t\leq 0.50$ mm), and $B_{as}=0.3$ (for 0.5 mm$<t$).

8. The method for predicting iron loss of a non-oriented electrical steel sheet after shearing according to any one of 2. to 7., wherein an upper limit $B_b$ for the mean magnetic flux density $B_0$ in the Region 2 is selected in a range of 1.45±0.15 T, and a ratio of increase in the magnetic flux density $B_1$ to increase in the mean magnetic flux density $B_0$ in the Region 2 is set to 1.02±0.015.

9. The method for predicting iron loss of a non-oriented electrical steel sheet after shearing according to any one of 2. to 8., wherein an upper limit $B_c$ for the mean magnetic flux density $B_0$ in the Region 3 is set to a value that is taken by the mean magnetic flux density $B_0$ when the magnetic flux density $B_1$ is equal to the magnetic flux density $B_2$, and a ratio of increase in the magnetic flux density $B_1$ to increase in the mean magnetic flux density $B_0$ in the Region 3 is set to 0.93±0.02.

10. The method for predicting iron loss of a non-oriented electrical steel sheet after shearing according to any one of 2. to 9., wherein a range in which the value of the mean magnetic flux density $B_0$ is greater than the upper limit $B_c$ is set as the Region 1.

Advantageous Effect

According to the present disclosure, it is possible to predict the iron loss properties of a non-oriented electrical steel sheet after shearing in a simpler and more accurate manner.

BRIEF DESCRIPTION OF THE DRAWING

In the accompanying drawings:

FIG. 6A illustrates a test piece combining steel sheets subjected to electric discharge machining, and FIG. 6B illustrates a test piece combining sheared steel sheets.

FIG. 8 illustrates the relationship, set in Experiment 2, between the mean magnetic flux density $B_0$ in each region and the magnetic flux density of the non-machining-affected zone $B_1$, the magnetic flux density of the machining affected zone $B_2$;

FIG. 14A represents a case where the sample thickness is 0.1 mm, FIG. 14B represents a case where the sample thickness is 0.2 mm.

DETAILED DESCRIPTION

Figure 1A:
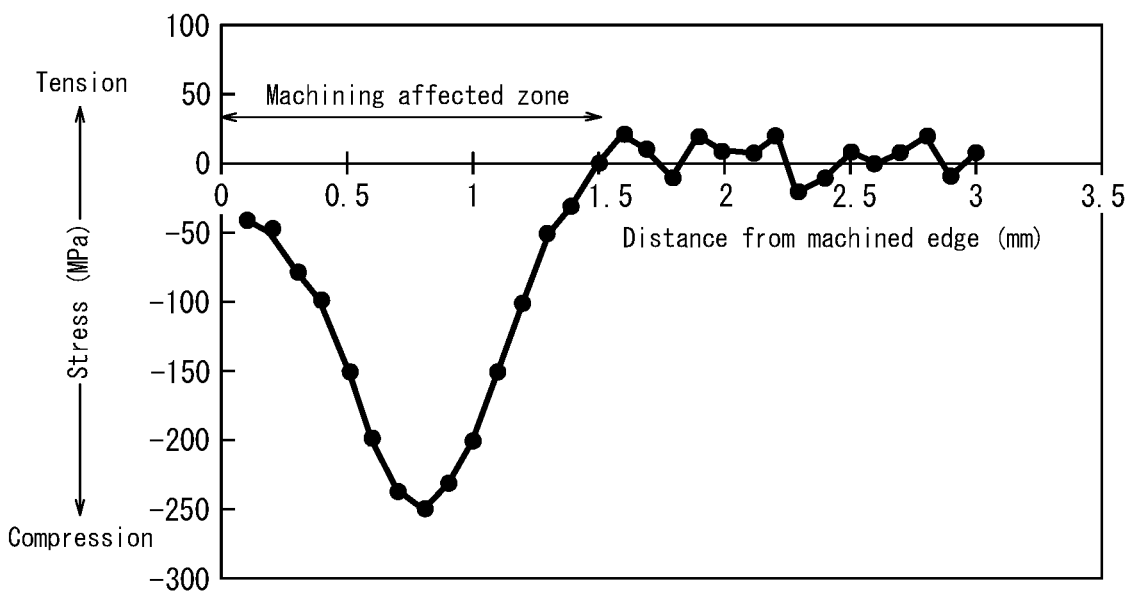
FIG. 1A illustrates the result of measuring by X-ray diffraction the residual stress distribution in a shear-cut sample near the machined edge.
Figure 1B:
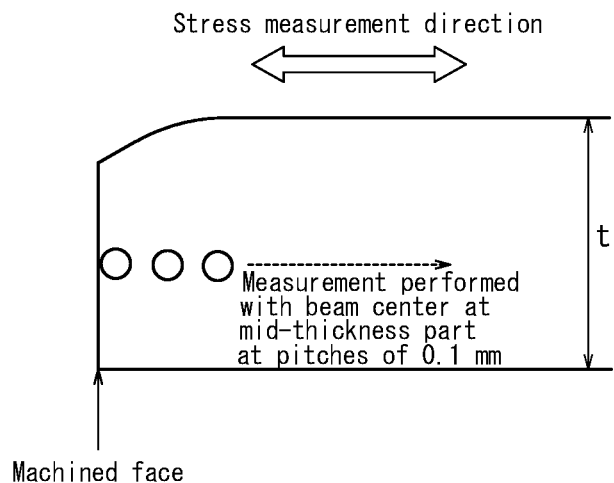
FIG. 1B illustrates the way in which the stress measurement was performed.
Figure 2:
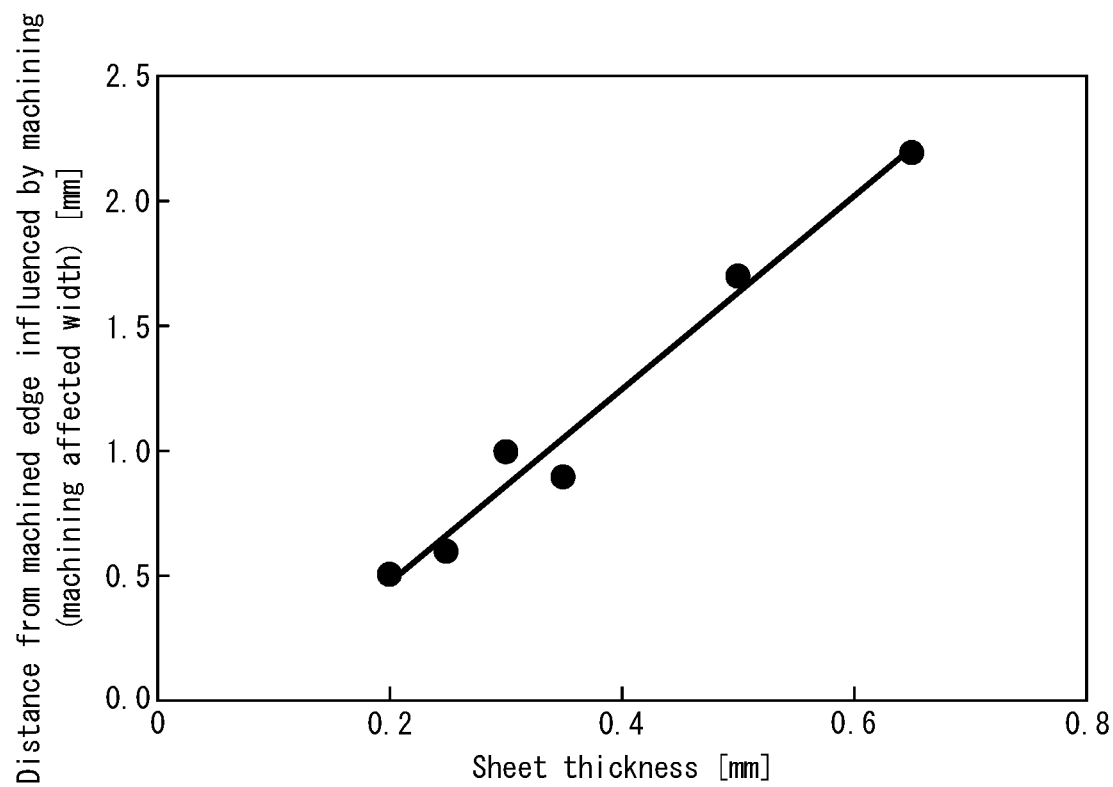
FIG. 2 illustrates the relationship between the sheet thickness of each shear-cut sample and the distance from the machined edge which is affected by the shearing (also referred to as "machining affected width")
Figure 3:
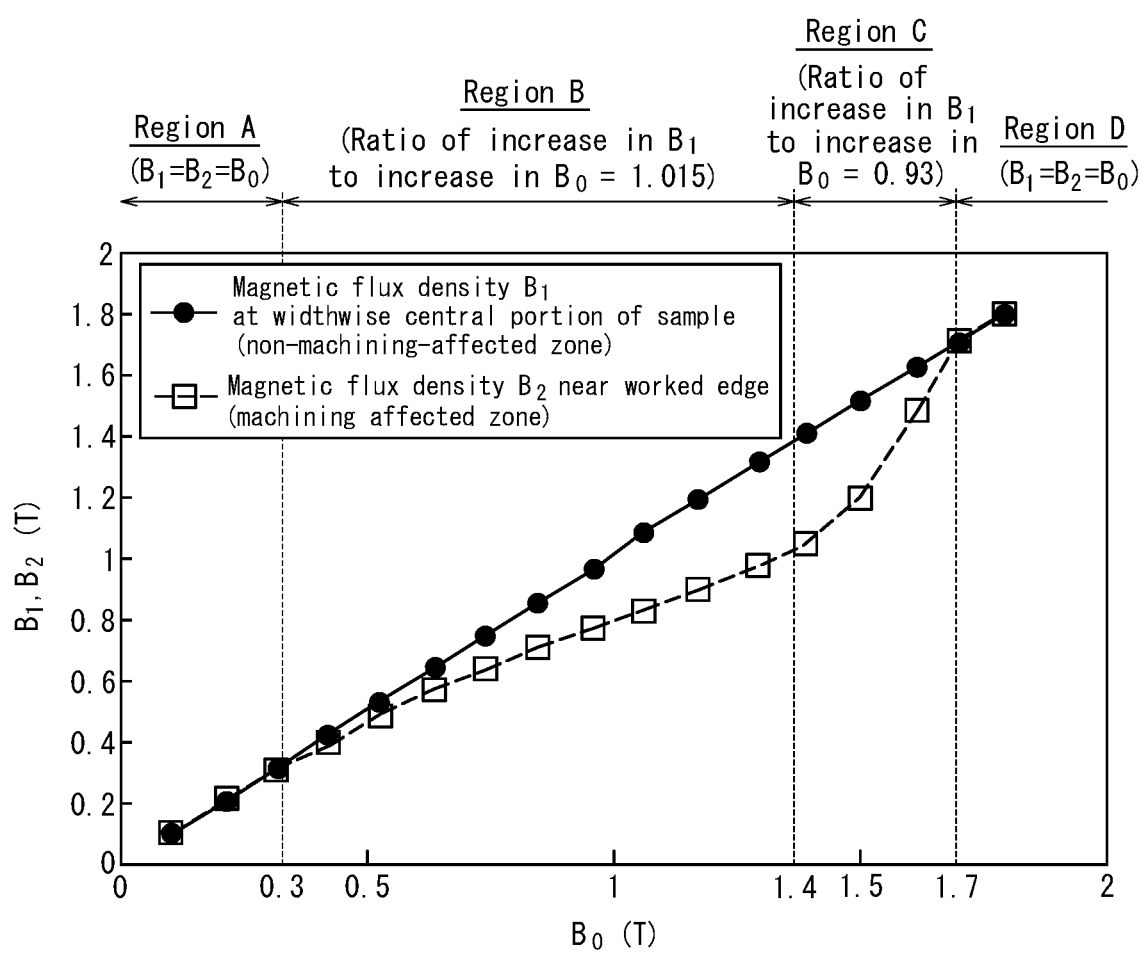
FIG. 3 illustrates the relationship between the mean magnetic flux density $B_0$ and the magnetic flux density of the non-machining-affected zone $B_1$ at the widthwise central portion of the sample, the magnetic flux density of the machining affected zone $B_2$ near the machined edge.
Figure 4:
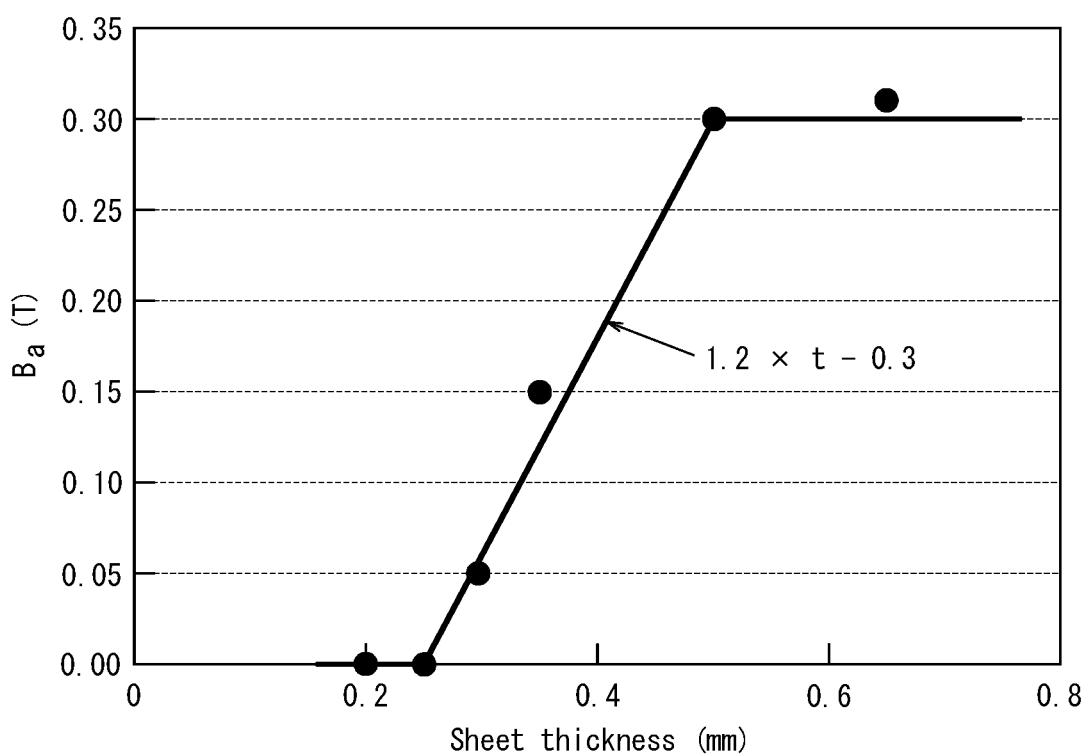
FIG. 4 illustrates the relationship between the sheet thickness of each shear-cut sample and the upper limit $B_a$ for the mean magnetic flux density in Region A.
Figure 5:
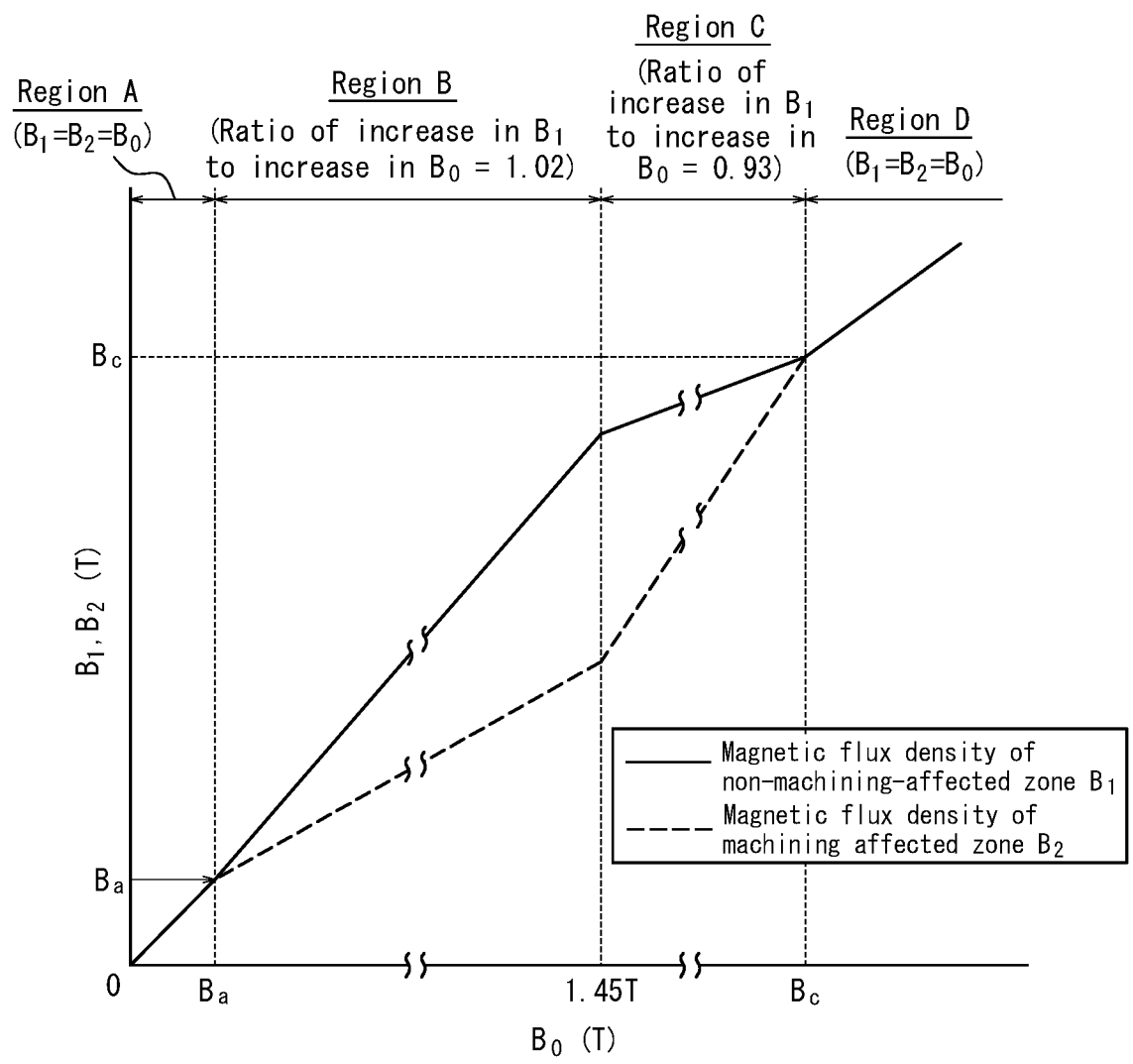
FIG. 5 illustrates the relationship between the mean magnetic flux density $B_0$ and the magnetic flux density of the non-machining-affected zone $B_1$, the magnetic flux density of the machining affected zone $B_2$, in a model developed from the results of Experiment 1.
Figure 6A:
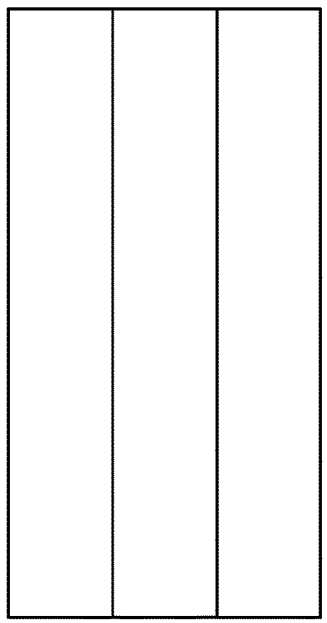
FIGS. 6A-6B are schematic views of test pieces used for Epstein measurement in Experiment 2.
Figure 6B:
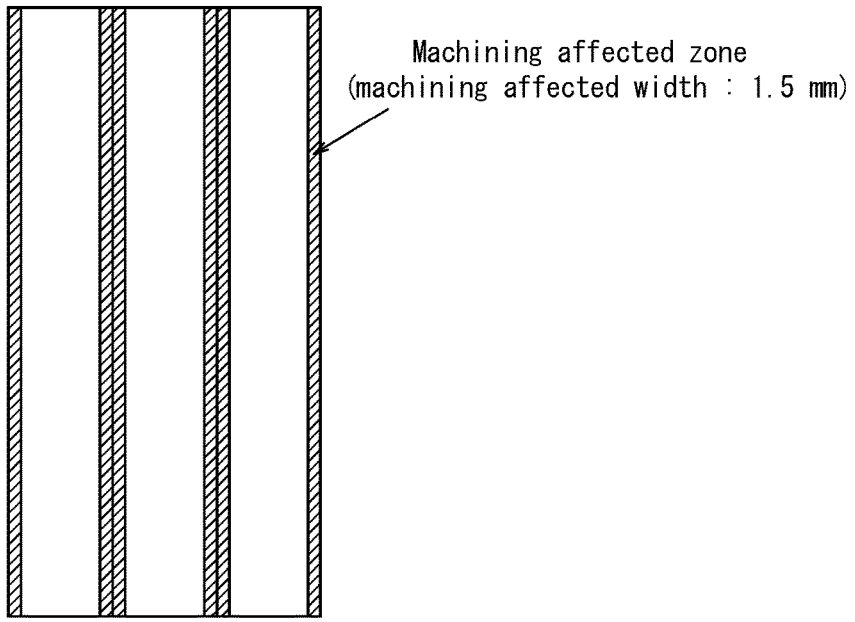
Figure 7:
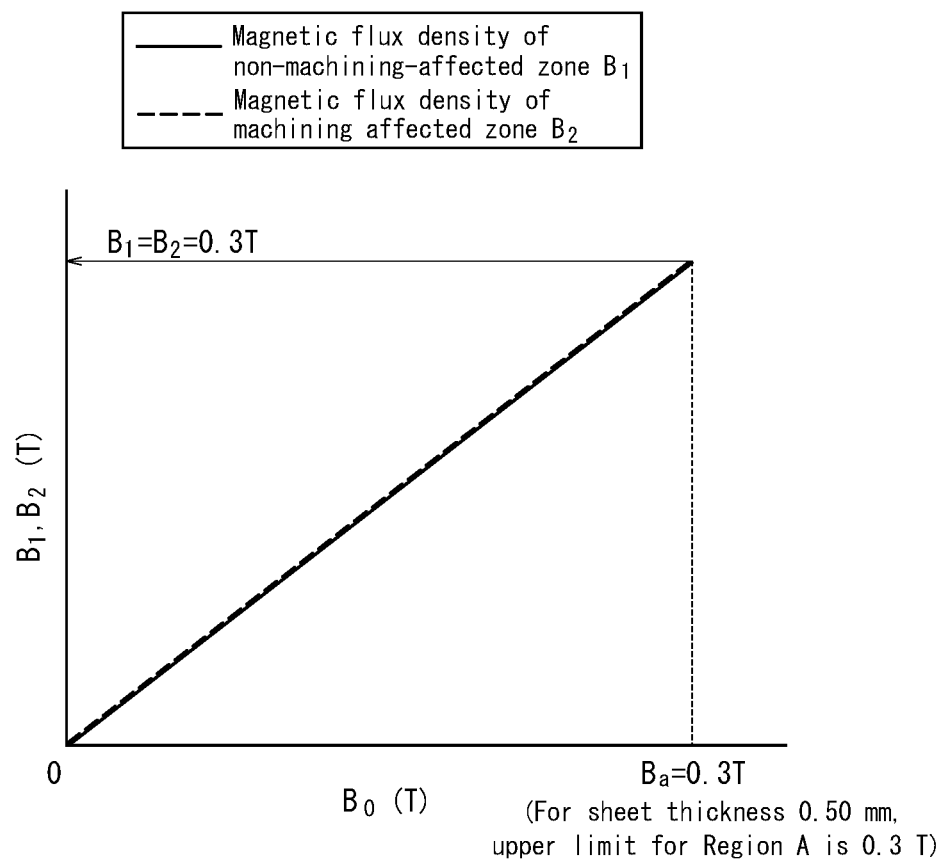
FIG. 7 illustrates the relationship, set in Experiment 2, between the mean magnetic flux density $B_0$ in Region A and the magnetic flux density of the non-machining-affected zone $B_1$, the magnetic flux density of the machining affected zone $B_2$.
Figure 9A:
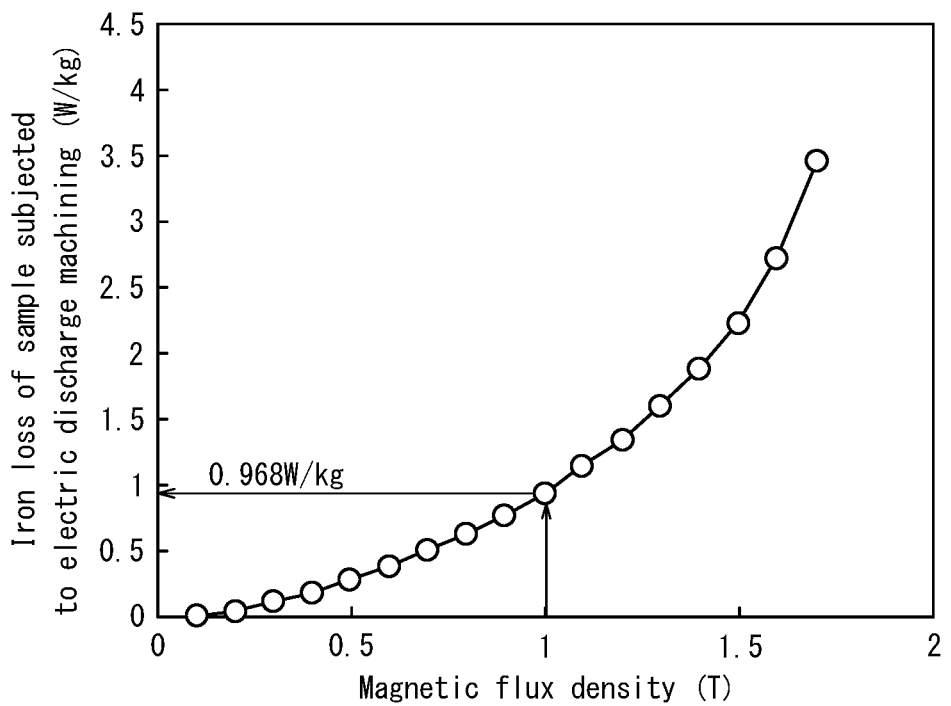
FIGS. 9A and 9B illustrate the magnetic property (iron loss) measurement results of samples subjected to electric discharge machining and of shear-cut samples, respectively.
Figure 9B:
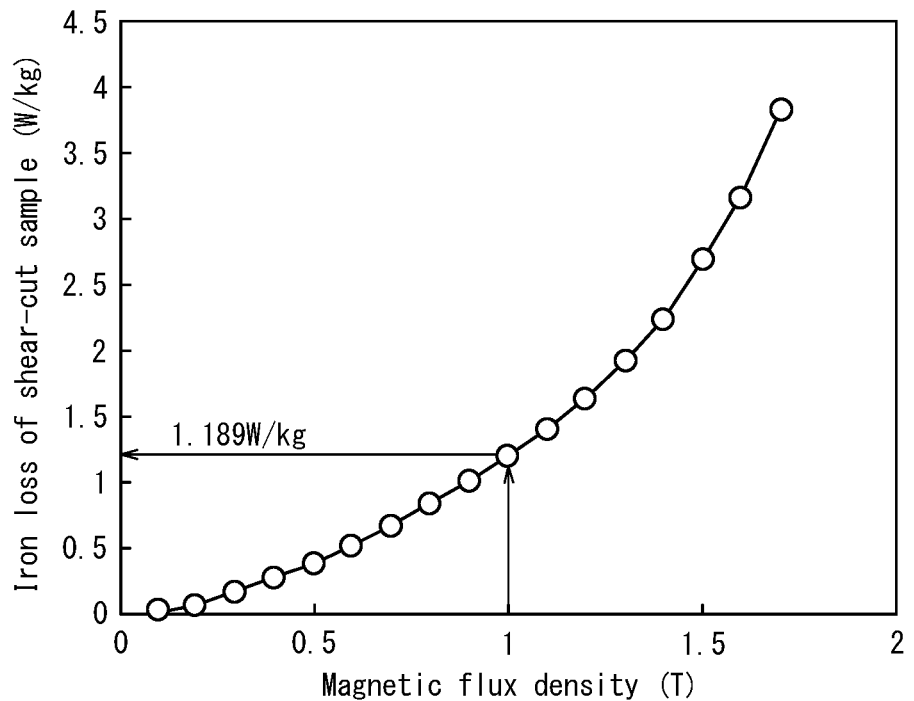
Figure 10:
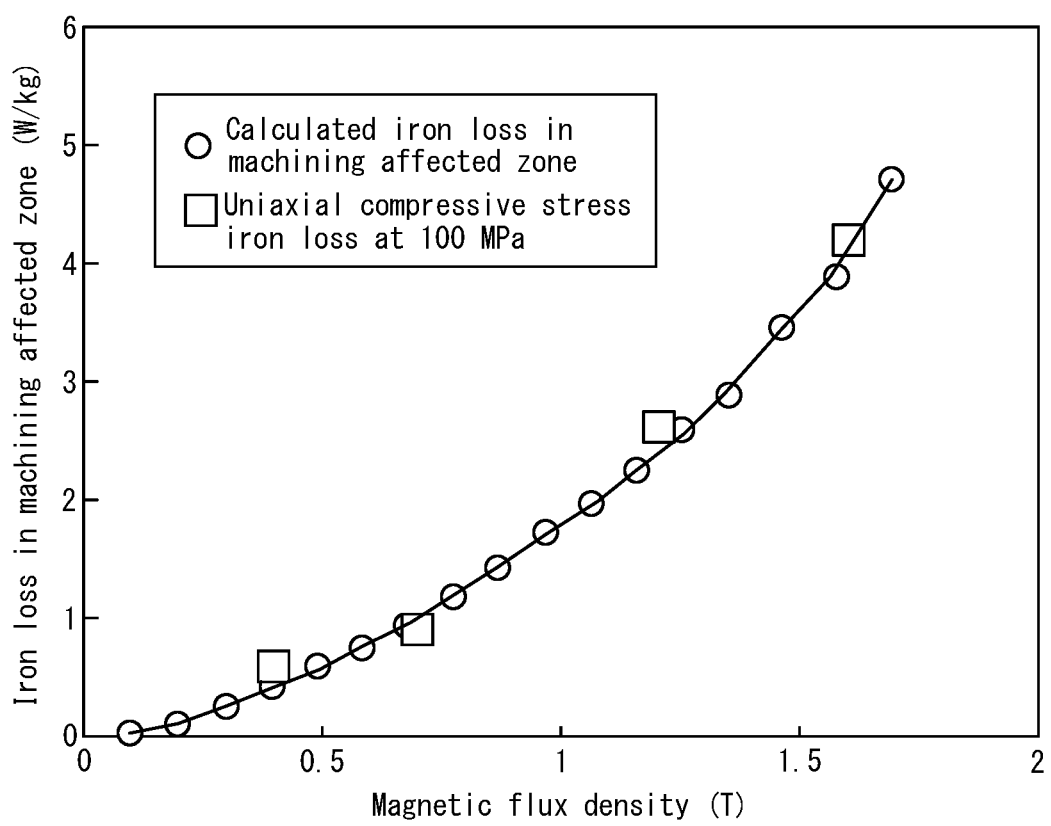
FIG. 10 illustrates the relationship between the iron loss properties at machining affected zones derived by calculation and the magnetic flux density.
Figure 11:
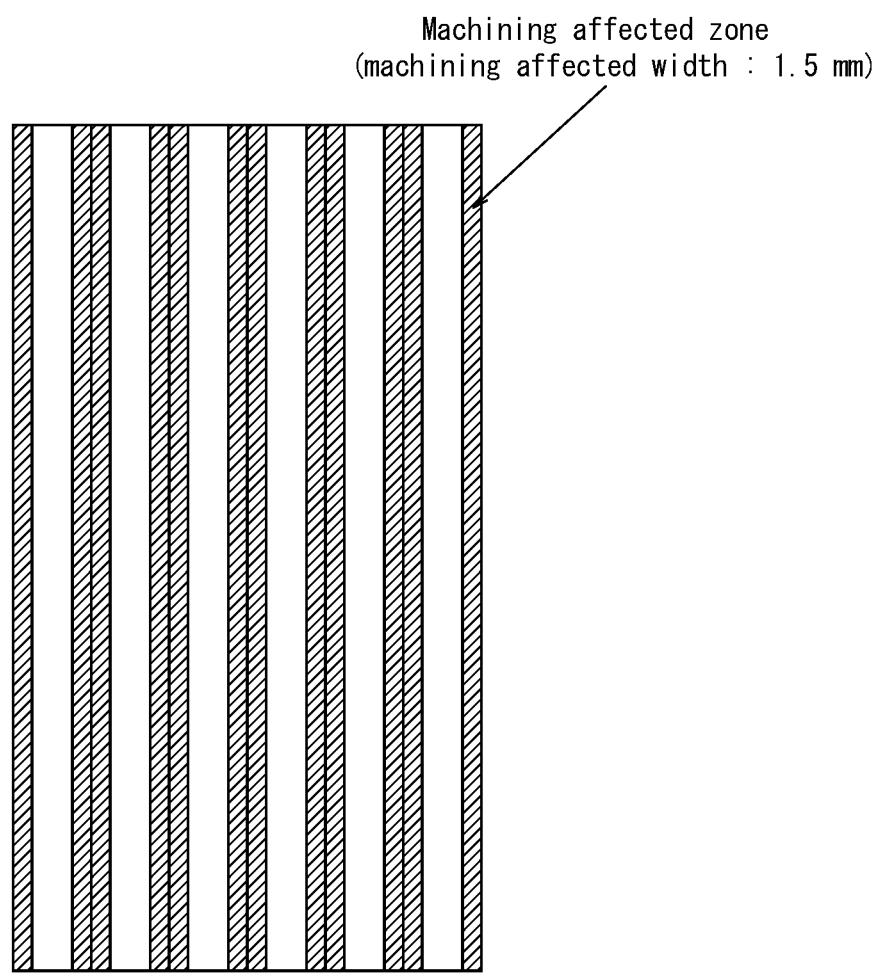
FIG. 11 is a schematic view of a test piece used for Epstein measurement in Experiment 3.
Figure 12:
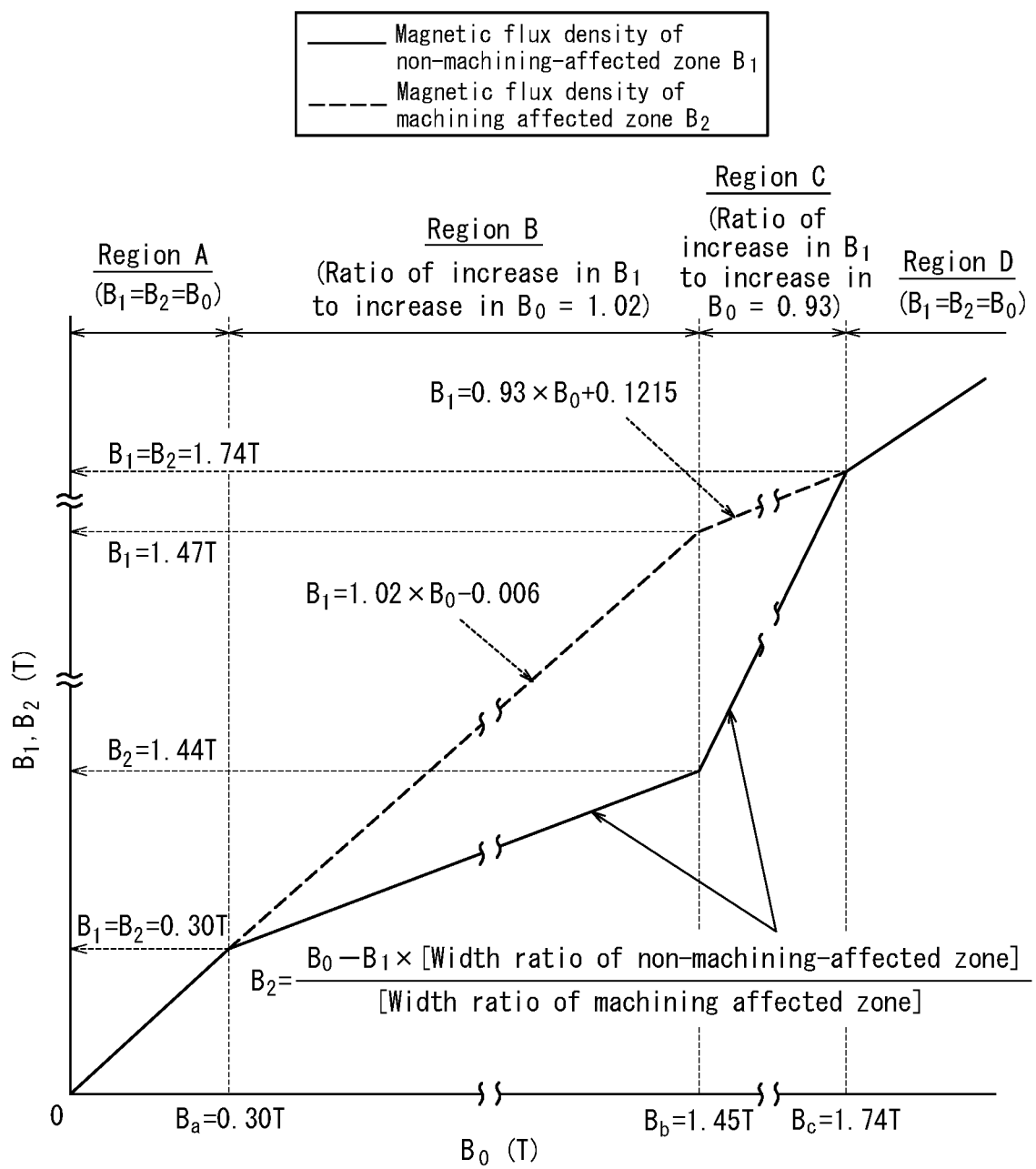
FIG. 12 illustrates the relationship, set in Experiment 3, between the mean magnetic flux density $B_0$ in each region and the magnetic flux density of the non-machining-affected zone $B_1$, the magnetic flux density of the machining affected zone $B_2$.
Figure 13:
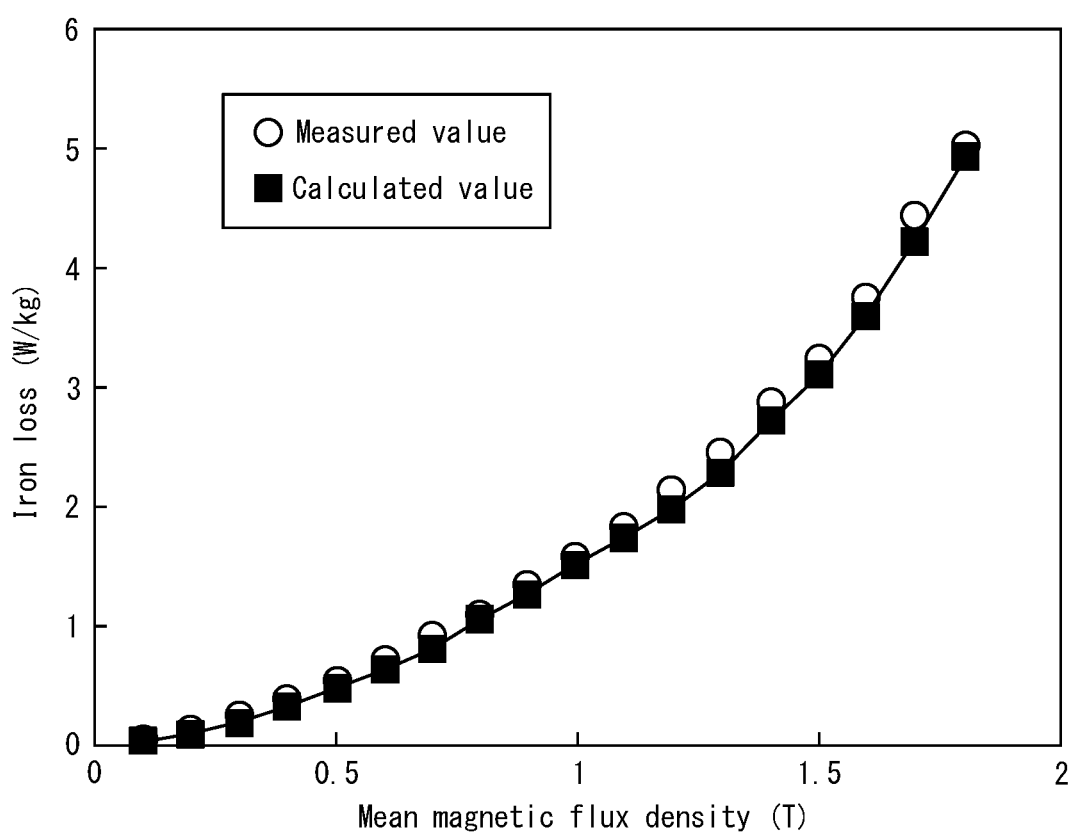
FIG. 13 is a plot of the calculated values and measured values of iron loss as a function of mean magnetic flux density $B_0$.
Figure 14A:
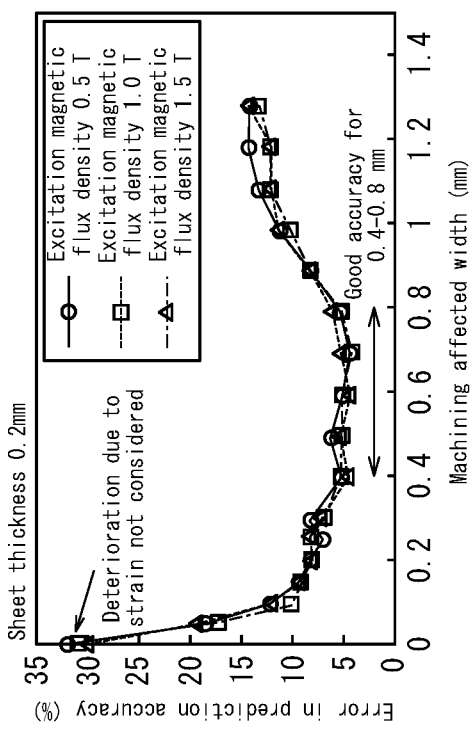
FIGS. 14A-14B illustrate the relationship between the machining affected width for each sample and the error in prediction accuracy.
Figure 14B:
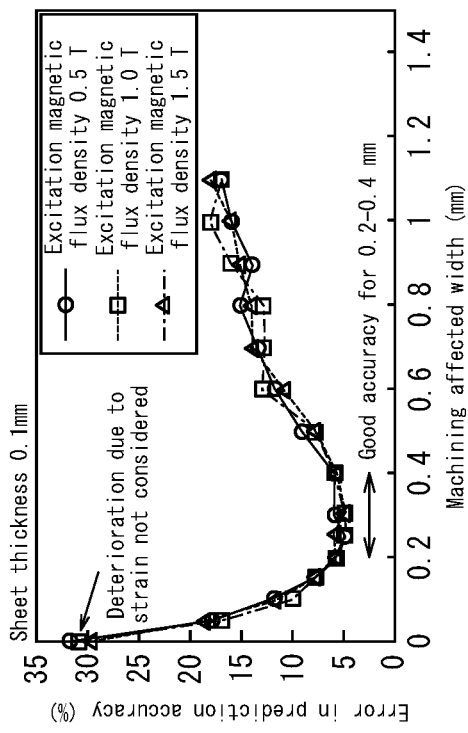
Figure 14C:
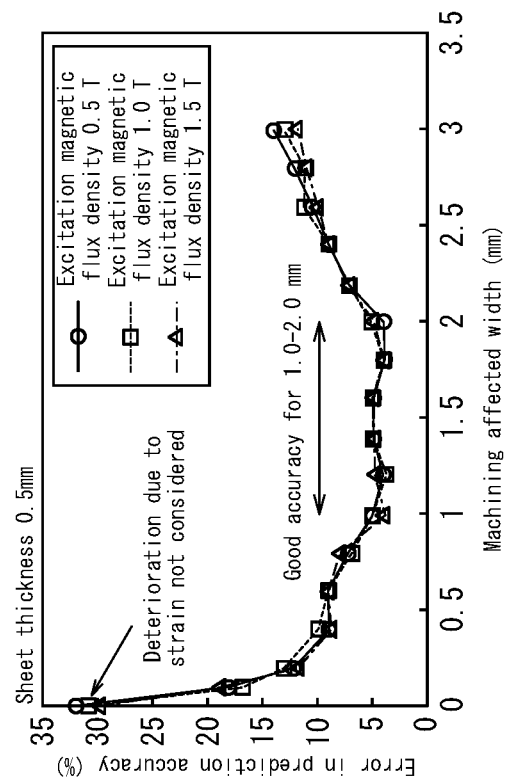
FIG. 14C represents a case where the sample thickness is 0.3 mm.
Figure 14D:
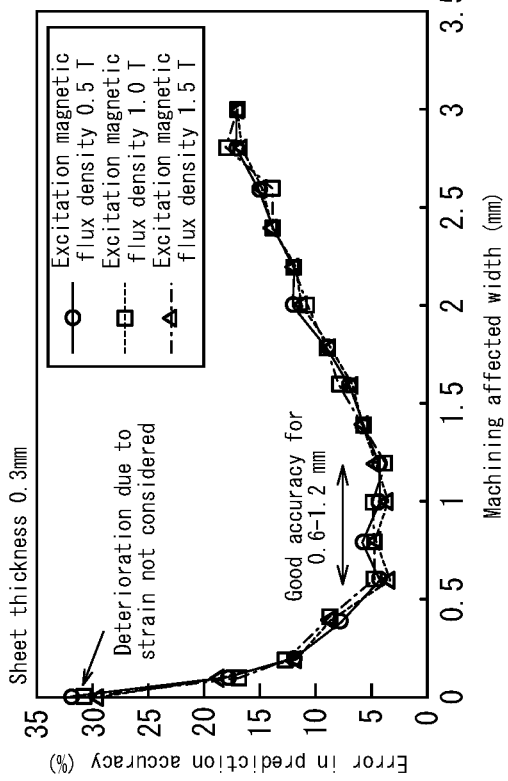
FIG. 14D represents a case where the sample thickness is 0.5 mm.

In the method for predicting iron loss of a non-oriented electrical steel sheet after shearing according to the present disclosure, the following points (a) to (g) are particularly important:

(a) The iron loss Wt of a non-oriented electrical steel sheet after shearing is derived by summing up the iron loss Wn of the machining affected zone to which machining strain is introduced by the shearing and the iron loss Wi of the non-machining-affected zone to which no machining strain is introduced, according to the width ratios of the non-machining-affected zone and of the machining affected zone; specifically, the iron loss Wt is derived by:

$Wt(B_0)=Wn(B_1)*$[a width ratio of the non-machining-affected zone]$+Wi(B_2)*$[a width ratio of the machining affected zone]

where $B_0$, $B_1$, and $B_2$ respectively denote a mean magnetic flux density of the non-oriented electrical steel sheet after shearing, a magnetic flux density of the non-machining-affected zone, and a magnetic flux density of the machining affected zone, upon excitation of the non-oriented electrical steel sheet after shearing, and where the width ratio of the non-machining-affected zone and the width ratio of the machining affected zone are a ratio of a total width of the non-machining-affected zone, and alternatively a ratio of a total width of the machining affected zone, to an entire width of the non-oriented electrical steel sheet after shearing, respectively.

The reason for using both the iron loss in the machining affected zone in which machining strain is introduced by the shearing and the iron loss in the non-machining-affected zone in which no machining strain is introduced is that the sample is not entirely but only partially affected by machining.

In addition, as the iron loss in the machining affected zone and the iron loss in the non-machining-affected zone, the iron loss at magnetic flux density $B_1$ and the iron loss at magnetic flux density $B_2$ described above, rather than mean magnetic flux density $B_0$, are respectively used. The reason is that the machining affected zone and the non-machining-affected zone have different magnetization properties, and the magnetic flux density is not necessarily the same in the machining affected zone and the non-machining-affected zone.

(b) Magnetic flux density distributions in the machining affected zone and in the non-machining-affected zone in the non-oriented electrical steel sheet after shearing are roughly classified into three models. Specifically, the relationships between mean magnetic flux density $B_0$ and magnetic flux densities $B_1$, $B_2$ are grouped into three regions depending on mean magnetic flux density $B_0$, namely Region 1 to Region 3 as defined below.

Region 1: A region in which as mean magnetic flux density $B_0$ increases, magnetic flux density of the non-machining-affected zone $B_1$ and magnetic flux density of the machining affected zone $B_2$ increase at the same rate (i.e., a region in which the magnetic flux flows in the machining affected zone in the same way as in the non-machining-affected zone).

Region 2: A region in which as mean magnetic flux density $B_0$ increases, magnetic flux density of the non-machining-affected zone $B_1$ increases at a higher rate than magnetic flux density of the machining affected zone $B_2$ (i.e., a region in which it is easy for the magnetic flux to flow in the non-machining-affected zone in relation to the mean magnetic flux density).

Region 3: A region in which as mean magnetic flux density $B_0$ increases, magnetic flux density of the machining affected zone $B_2$ increases at a higher rate than magnetic flux density of the non-machining-affected zone $B_1$ (i.e., a region in which it is difficult for the magnetic flux to flow in the non-machining-affected zone in relation to the mean magnetic flux density).

The reason for this limitation is that these models match well with the measured results of the probe coil method despite their simplicity.

Regions 1 to 3 are generally classified as follows.

Region 1: A low-magnetic flux density region (Region A) in which the mean magnetic flux density ranges from 0 T to $B_a$ T.

A high-magnetic flux density region (Region D) in which the mean magnetic flux density is higher than $B_a$ T.

Region 2: A region (Region B) in which the mean magnetic flux density ranges from $B_a$ T to $B_b$ T (higher than $B_a$ T and no higher than $B_b$ T), and in which it is more easy for the magnetic flux to flow in the non-machining-affected zone than in the machining affected zone.

Region 3: A region (Region C) in which the mean magnetic flux density ranges from $B_b$ T to $B_c$ T (higher than $B_b$ T and no higher than $B_c$ T), and in which it is more difficult for the magnetic flux to flow in the non-machining-affected zone than in the machining affected zone.

However, $B_a$ may be set to 0 T ($B_a$=0 T) depending on the sheet thickness of the steel sheet to be predicted.

(c) As the iron loss in the non-machining-affected zone in which no machining strain is introduced, it is optimal to use the iron loss of a sample prepared by electric discharge machining or the like in which the influence exerted by machining is almost negligible However, a simpler setup may substitute this iron loss by the iron loss of a sample sheared (shear-cut) to a width of 30 mm or more (preferably 100 mm or more), in which case the iron loss of the non-oriented electrical steel sheet can still be predicted without significant loss in prediction accuracy.

The reason for the possibility of substitution of the iron loss of the non-machining-affected zone by the iron loss of a sample sheared to a width of 30 mm or more is considered to be that the machining affected zone accounts for a small proportion of the sample having an entire width of 30 mm or more.

(d) The iron loss in the machining affected zone can be derived from the comparison between iron losses of two samples of the same material with different degrees of influence exerted by the shearing (for example, between the iron loss of a sample in which the influence exerted by machining is almost negligible, or a sample subjected to electric discharge machining, and the iron loss of a sample shear-cut to an arbitrary width, or between iron losses of two samples shear-cut to different widths).

In particular, when comparing iron losses of two samples of different widths to derive iron loss in the machining affected zone, the iron loss can be predicted with higher accuracy if two samples as described below are used: one sheared to a width of 30 mm or more with a small degree of influence exerted by machining (i.e., the proportion of the entire sample accounted for by the machining affected zone is small) and the other sheared to a width of 15 mm or less with a large degree of influence exerted by machining (i.e., the proportion of the entire sample accounted for by the machining affected zone is large).

The reason for this is considered as follows. As the differences in the influence exerted by machining strain between two samples increase, the variation in iron loss resulting from the machining becomes more significant and the impact of other factors on the variation of iron loss is moderated accordingly. This is considered to reduce variations attributable to other factors, and therefore enables highly accurate prediction.

From the perspective of making more accurate prediction, the width of the sample with a small degree of influence exerted by machining is preferably 100 mm or more. The upper limit is not particularly limited, yet it is usually about 500 mm. The width of the sample with a large degree of influence exerted by machining is preferably 10 mm or less. The lower limit is not particularly limited, yet it is usually about 2 mm.

More specifically, using the iron loss $W_{s1}(B_0)$ of a sample sheared to a width of 15 mm or less and the iron loss $W_{s2}(B_1)$ of a sample sheared to a width of 30 mm or more, provided that both samples are made of the same material, the iron loss $Wi(B_2)$ in the machining affected zone can be derived from:

$$Wi(B_2)=(W_{s1}(B_0)-W_{s2}(B_1))*[\text{a width ratio of the non-machining-affected zone in a sample having a machining width of 30 mm or more}]/[\text{a width ratio of the machining affected zone in a sample having a machining width of 15 mm or less}]$$

(e) The iron loss of the machining affected zone may also be substituted by the iron loss as measured upon a uniaxial compressive stress of 100 MPa or more being applied to another non-oriented electrical steel sheet of the same material as the steel sheet to be predicted.

The reason for this is thought to be that although an actual machining affected zone has a complicated stress distribution, uniaxial compressive stress characteristics at 100 MPa or more tend to reach saturation and do not cause a significant change in iron loss, and that the direction of stress field is not of particular relevance in a region with an extensive stress field profile in which iron loss tends to reach a plateau, and the stress distribution may saturate at a certain value.

The upper limit for uniaxial compressive stress to be added is not particularly limited, yet it is usually about 300 MPa.

(f) Since a machining affected width (machining affected range) in the non-oriented electrical steel sheet after shearing includes not only a plastic strain introduction range but also an elastic strain introduction range, it is preferable to determine a machining affected width from elastic stress analysis using X-rays or synchrotron radiation.

However, in a simpler setup, it suffices for the machining affected width to be set to a value that is two to four times the sheet thickness of the steel sheet. This enables estimation of the iron loss of the non-oriented electrical steel sheet after shearing without significantly degrading the accuracy.

The reason for degradation in the prediction accuracy of iron loss when the machining affected width deviates from two to four times the thickness of the steel sheet is considered to be that the deviation from the actual elastic strain range becomes more pronounced.

(g) In the case of setting Region 1 (Region A), which is set as the above-described low-magnetic flux density region, in a range in which mean magnetic flux density $B_0$ ranges from 0 T to $B_a$ T, it is preferable that reference value $B_{as}$ for $B_a$ according to the sheet thickness t is derived from the following equation and $B_a$ is selected from the derived reference value $B_{as} \pm 0.2$ T (more preferably, in a range of $B_{as} \pm 0.1$ T). With this setup, the iron loss of the non-oriented electrical steel sheet after shearing can be predicted with high accuracy.

$B_{as}=0$ (for $t \leq 0.25$ mm), $B_{as}=1.2*t-0.3$ (for 0.25 mm$<t \leq 0.50$ mm), and $B_{as}=0.3$ (for 0.5 mm$<t$).

In setting Region 2 (Region B), $B_b$ is preferably selected in a range of $1.45 \pm 0.15$ T (more preferably, in a range of $1.45 \pm 0.1$ T). With this setup, the iron loss of the non-oriented electrical steel sheet after shearing can be predicted with high accuracy.

The reason why the prediction accuracy of iron loss improves when $B_a$ and $B_b$ are set in the above ranges is considered to be that our models more closely approximate the actual behavior of magnetic flux.

In addition, the ratio of increase in the magnetic flux density of the non-machining-affected zone to increase in mean magnetic flux density $B_0$ in Region 2 (Region B) is preferably set to $1.02 \pm 0.015$ (more preferably, $1.02 \pm 0.01$).

Moreover, the ratio of increase in the magnetic flux density of the non-machining-affected zone to increase in $B_0$ in Region 3 (Region C) is preferably set to $0.93 \pm 0.02$ (more preferably, $0.93 \pm 0.01$).

$B_c$ can be set as the mean magnetic flux density when $B_1=B_2$ in Region C.

Conditions other than those described above, for example, materials to be used, methods of manufacturing the same, and the like are not particularly limited, and the setup disclosed herein may be applied to any conventionally known non-oriented electrical steel sheets.

No limitation is placed on the width of the steel sheet to be predicted (the width of the steel sheet after shearing), yet it is particularly suitable that the setup disclosed herein be used for prediction of iron loss properties of a steel sheet after shearing whereby the steel sheet is sheared in particular to a width of 1 mm or more and less than 30 mm, and more preferably to a width of 20 mm or less.

As mentioned above, the term "shearing" used herein refers to broadly-construed shear processing including shear cutting, punching, and the like. Although the above experiments have been described in the context of shearing being shear cutting, our iron loss prediction method is also applicable to any processing, involving shearing to cause strain in the steel sheet, that corresponds to broadly-construed shear processing such as punching. Other conditions such as processing conditions are not particularly limited, and conventional methods may be followed.

Additionally, methods for measuring iron loss properties of each sample (for obtaining measured values) include, but are not limited to, Epstein measurements, single sheet tester (SST) measurements, and ring measurements.

As samples for which iron losses in non-machining-affected zones and in machining affected zones are predicted, steel sheets of the same material as the steel sheet for iron loss prediction are used. As used herein, "steel sheets of the same material" are not limited to steel sheets that are completely identical in composition, yet include, for example, steel sheets that contain the same components and for which the difference in the contents of the main components, such as Si, Al, and Mn, excluding incidental impurities, is within 0.2 mass % each.

EXAMPLES

Example 1

Iron loss prediction was performed on non-oriented electrical steel sheets after shearing. In this case, non-oriented electrical steel sheets of 0.35 mm in sheet thickness were sheared (shear-cut) to respective widths as listed in "Sample width for prediction" in Table 9.

Iron losses of the steel sheets sheared to respective widths were predicted by varying parameters as listed in Table 9, such as methods for estimation of iron losses after shearing, methods for derivation of iron losses in machining affected zones, methods for derivation of iron losses in non-machining-affected zones, and magnetic flux density distributions in machining affected zones and in non-machining-affected zones, and then comparing the predicted values with the measured values.

The magnetic flux density distributions in non-machining-affected zones and machining affected zones of the non-oriented electrical steel sheets after shearing were classified into and set in any of the following regions: Region A corresponding to Region 1 in which the mean magnetic flux density ranges from 0 T to $B_a$ T; Region B corresponding to Region 2 in which the mean magnetic flux density ranges from $B_a$ T to $B_b$ T (higher than $B_a$ T and no higher than $B_b$ T); Region C corresponding to Region 3 in which the mean magnetic flux density ranges from $B_b$ T to $B_c$ T (higher than $B_b$ T and no higher than $B_c$ T); and Region D corresponding to Region 1 in which the mean magnetic flux density is higher than $B_c$ T. The values were varied for $B_a$ and $B_b$, as well as for the ratio of increase in magnetic flux density $B_1$ to increase in mean magnetic flux density $B_0$, which ratio represents the easiness of flow of magnetic flux in the non-machining-affected zones in Regions B and C.

For each sample for iron loss prediction, a test piece was prepared with a total width of 30 mm by combining multiple samples sheared (shear-cut) to respective widths, then a total of eight test pieces were prepared with their longitudinal direction in parallel to either the rolling direction (L direction) or the transverse direction (C direction), and the iron loss of the sample was determined using the results from performing Epstein measurements on a total of eight L+C-direction test pieces (four in the L direction and four in the C direction).

Regarding the uniaxial compressive stress iron loss properties, the iron loss of each sample was determined by averaging the results from measuring single-sheet iron losses of individual steel sheets, whose longitudinal direction was in parallel to the L and C directions, upon excitation of each steel sheet as a single sheet under a stress of 100 MPa along the excitation direction, and finally performing corrections on the measured iron losses to make them equivalent to the corresponding Epstein values, based on the values of the individual steel sheets and Epstein values determined under no stress.

Additionally, regarding the measured value of iron loss of each steel sheet to be predicted, samples (280 mm long) were sheared (shear-cut) from the steel sheet to respective widths and attached together to have a total width of 30 mm, then four such samples were prepared with their longitudinal direction parallel to the rolling direction (L direction) and another four with their longitudinal direction parallel to the transverse direction (C direction), then a total of eight L+C-direction samples were subjected to Epstein measurement, and the measurement results were used to determine the measured value of iron loss of the steel sheet to be predicted.

The evaluation results are also listed in Table 9.

TABLE 9

| No. | Value set for machining affected width of sample to be predicted (mm) | Sample used in prediction of iron loss in non-machining-affected zone | Sample used in derivation of iron loss in machining affected zone | Value set for mean magnetic flux density as a boundary value between respective regions $B_a$ (T) | $B_b$ (T) | $B_a$ to $B_{as}$ (T) | $B_b$ to 1.45 (T) | Value set for the ratio* of increse in magnetic flux density of non-machining-affected zone in Region B | Value set for the ratio* of increse in magnetic flux density of non-machining-affected zone in Region C |
|---|---|---|---|---|---|---|---|---|---|
| 1 | In this case, a value as conventionally measured according to JIS C 2550 at a width of 30 mm was used as a predicted value. | | | | | | | | |
| 2 | 2.5 times the sheet thickness | Sample subjected to electric discharge machining | (i) Sample subjected to electric discharge machining (ii) Sample shear-cut to width of 10 mm | 0.2135 | 1.65 | 0.1 | 0.2 | 1.1 | 0.93 |
| 3 | 2.5 times the sheet thickness | Sample subjected to electric discharge machining | (i) Sample subjected to electric discharge machining (ii) Sample shear-cut to width of 10 mm | 0.2135 | 1.5 | 0.1 | 0.05 | 1.02 | 0.85 |
| 4 | 2.5 times the sheet thickness | Sample subjected to electric discharge machining | (i) Sample subjected to electric discharge machining (ii) Sample shear-cut to width of 10 mm | 0.1135 | 1.45 | 0 | 0 | 1.05 | 0.93 |
| 5 | 2.5 times the sheet thickness | Sample shear-cut to width of 30 mm | (i) Sample shear-cut to width of 30 mm (ii) Sample shear-cut to width of 5 mm | 0.0635 | 1.5 | −0.05 | 0.05 | 1.005 | 0.99 |
| 6 | 2.5 times the sheet thickness | Sample shear-cut to width of 30 mm | (i) Sample shear-cut to width of 30 mm (ii) Sample shear-cut to width of 5 mm | 0.4135 | 1.5 | 0.3 | 0.05 | 1 | 0.93 |
| 7 | 3.5 times the sheet thickness | Sample shear-cut to width of 30 mm | In this case, iron loss properties upon application of a uniaxial compressive stress of 100 MPa were used. | 0.0635 | 1.47 | −0.05 | 0.02 | 1.015 | 0.94 |
| 8 | Measured value | Sample subjected to electric discharge machining | (i) Sample subjected to electric discharge machining (ii) Sample shear-cut to width of 10 mm | 0.3635 | 1.3 | 0.25 | −0.15 | 1.015 | 0.92 |

TABLE 9-continued

| | | Sample shear-cut to width of 30 mm | | | | | | Sample shear-cut to width of 15 mm | | | | | |
|---|---|---|---|---|---|---|---|---|---|---|---|---|---|
| 9 | 5 times the sheet thickness | (i) Sample shear-cut to width of 30 mm (ii) Sample shear-cut to width of 20 mm | 0.1635 | 1.5 | 0.05 | 0.05 | 1.025 | 0.93 | | | | | |
| 10 | Measured value | (i) Sample subjected to electric discharge machining (ii) Sample shear-cut to width of 15 mm | 0.0135 | 1.5 | −0.1 | 0.05 | 1.025 | 0.93 | | | | | |

| No. | Sample width for prediction (mm) | Error in prediction accuracy of iron loss at each excitation magnetic flux density (at 50 Hz) [%] | | | | | | | | | | Remarks |
|---|---|---|---|---|---|---|---|---|---|---|---|---|
| | | 0.15 T | 0.35 T | 0.55 T | 0.75 T | 0.95 T | 1.15 T | 1.35 T | 1.55 T | 1.75 T | 1.85 T | |
| 1 | 7.5 | 35 | 28 | 40 | 31 | 34 | 35 | 31 | 28 | 30 | 29 | Comp. Ex. |
| 2 | 7.5 | 8 | 16 | 15 | 18 | 15 | 16 | 15 | 18 | 18 | 18 | Ex. |
| 3 | 7.5 | 8 | 6 | 5 | 5 | 5 | 5 | 5 | 13 | 14 | 16 | Ex. |
| 4 | 7.5 | 5 | 4 | 5 | 6 | 4 | 5 | 4 | 5 | 5 | 5 | Ex. |
| 5 | 10 | 5 | 4 | 4 | 5 | 6 | 6 | 5 | 14 | 15 | 15 | Ex. |
| 6 | 10 | 4 | 10 | 14 | 15 | 16 | 16 | 16 | 16 | 16 | 16 | Ex. |
| 7 | 5 | 6 | 6 | 5 | 7 | 7 | 5 | 5 | 5 | 5 | 5 | Ex. |
| 8 | 7.5 | 5 | 15 | 15 | 16 | 13 | 14 | 15 | 15 | 18 | 17 | Ex. |
| 9 | 15 | 17 | 17 | 18 | 18 | 17 | 18 | 18 | 19 | 16 | 16 | Ex. |
| 10 | 5 | 16 | 18 | 17 | 16 | 16 | 15 | 16 | 16 | 15 | 15 | Ex. |

*The ratio of increase in magnetic flux density of non-machining-affected zone $B_I$ to increase in mean magnetic flux density $B_0$.

It can be seen from Table 9 that in all of our examples, the error in prediction accuracy is 20% or lower, indicating that the iron loss can be predicted with high accuracy. In particular, it will be appreciated that for Examples No. 4 and 7 in which all the parameters were set under suitable conditions, the error in prediction accuracy is 10% or lower in every magnetic flux density region, where the iron loss can be predicted with very high accuracy.

In contrast, significant errors can be found in every magnetic flux density region for Comparative Example No. 1 in which the iron loss of a sample sheared to a width of 30 mm as measured in accordance with JIS C 2550 was applied as the predicted value without considering the influence of the machining strain.

Example 2

Iron loss prediction was performed on non-oriented electrical steel sheets after shearing. In this case, non-oriented electrical steel sheets of 0.35 mm in sheet thickness were sheared (shear-cut) to respective widths as listed in "Sample width for prediction" in Table 10.

As in Example 1, iron losses of the steel sheets sheared to respective widths were predicted by varying parameters as listed in Table 10, such as methods for estimation of iron losses after shearing, methods for derivation of iron losses in machining affected zones, methods for derivation of iron losses in non-machining-affected zones, and magnetic flux density distributions in machining affected zones and in non-machining-affected zones, and then comparing the predicted values with the measured values.

For each sample for iron loss prediction, a test piece was prepared with a total width of 48 mm by combining multiple samples sheared (shear-cut) to respective widths, then a total of four such test pieces were prepared with their longitudinal direction in parallel to the transverse direction, and the iron loss of each sample was determined by averaging the results from measuring single-sheet iron losses of the individual test pieces one by one using a single sheet test (SST) measuring frame.

Additionally, regarding the measured value of iron loss of each steel sheet to be predicted, samples (280 mm long) were sheared (shear-cut) from the steel sheet to respective widths and attached together to have a total width of 48 mm, then a total of four samples were prepared with their longitudinal direction parallel to the transverse direction, and the measured value of iron loss of the steel sheet was determined by averaging the results from measuring single-sheet iron losses of the individual samples one by one using a single sheet test (SST) measuring frame.

The uniaxial compressive stress iron loss properties were determined similarly as in Example 1.

The evaluation results are also listed in Table 10.

TABLE 10

| No. | Value set for machining affected width of sample to be predicted (mm) | Sample used in prediction of iron loss in non-machining-affected zone | Sample used in derivation of iron loss in machining affected zone | Value set for mean magnetic flux density as a boundary value between respective regions $B_a$ (T) | $B_b$ (T) | $B_a$ to $B_{as}$ (T) | $B_b$ to 1.45 (T) | Value set for the ratio* of increse in magnetic flux density of non-machining-affected zone in Region B | Value set for the ratio* of increse in magnetic flux density of non-machining-affected zone in Region C |
|---|---|---|---|---|---|---|---|---|---|
| 1 | In this case, a value as conventionally measured according to JIS C 2550 at a width of 30 mm was used as a predicted value. | | | | | | | | |
| 2 | 2.2 times the sheet thickness | Sample subjected to electric discharge machining | (i) Sample subjected to electric discharge machining (ii) Sample shear-cut to width of 6 mm | 0.1 | 1.65 | 0.1 | 0.2 | 1.1 | 0.93 |
| 3 | 2.2 times the sheet thickness | Sample subjected to electric discharge machining | (i) Sample subjected to electric discharge machining (ii) Sample shear-cut to width of 6 mm | 0.1 | 1.5 | 0.1 | 0.05 | 1.02 | 0.85 |
| 4 | 2.2 times the sheet thickness | Sample subjected to electric discharge machining | (i) Sample subjected to electric discharge machining (ii) Sample shear-cut to width of 6 mm | 0 | 1.45 | 0 | 0 | 1.05 | 0.93 |
| 5 | 3 times the sheet thickness | Sample shear-cut to width of 48 mm | (i) Sample shear-cut to width of 48 mm (ii) Sample shear-cut to width of 12 mm | 0 | 1.5 | 0 | 0.05 | 1.005 | 0.99 |
| 6 | 3 times the sheet thickness | Sample shear-cut to width of 48 mm | (i) Sample shear-cut to width of 48 mm (ii) Sample shear-cut to width of 12 mm | 0.3 | 1.5 | 0.3 | 0.05 | 1 | 0.93 |
| 7 | 3.8 times the sheet thickness | Sample shear-cut to width of 48 mm | In this case, iron loss properties upon application of a uniaxial compressive stress of 100 MPa were used. | 0 | 1.47 | 0 | 0.02 | 1.015 | 0.94 |
| 8 | Measured value | Sample subjected to electric discharge machining | (i) Sample subjected to electric discharge machining (ii) Sample shear-cut to width of 8 mm | 0.25 | 1.3 | 0.25 | −0.15 | 1.015 | 0.92 |

TABLE 10-continued

| | | | | | | | | | | |
|---|---|---|---|---|---|---|---|---|---|---|
| 9 | 4.5 times the sheet thickness | Sample shear-cut to width of 48 mm | (i) Sample shear-cut to width of 48 mm (ii) Sample shear-cut to width of 12 mm | 0.05 | 1.5 | 0.05 | 0.05 | 0.05 | 1.025 | 0.93 |
| 10 | Measured value | Sample shear-cut to width of 12 mm | (i) Sample subjected to electric discharge machining (ii) Sample shear-cut to width of 12 mm | 0 | 1.5 | 0 | 0.05 | 0.05 | 1.025 | 0.93 |

| No. | Sample width for prediction (mm) | Error in prediction accuracy of iron loss at each excitation magnetic flux density (at 50 Hz) [%] | | | | | | | | | | Remarks |
|---|---|---|---|---|---|---|---|---|---|---|---|---|
| | | 0.15 T | 0.35 T | 0.55 T | 0.75 T | 0.95 T | 1.15 T | 1.35 T | 1.55 T | 1.75 T | 1.85 T | |
| 1 | 12 | 34 | 30 | 38 | 33 | 31 | 30 | 34 | 30 | 35 | 32 | Comp. Ex. |
| 2 | 12 | 16 | 15 | 18 | 17 | 16 | 15 | 20 | 15 | 15 | 15 | Ex. |
| 3 | 12 | 7 | 5 | 4 | 6 | 7 | 7 | 7 | 15 | 14 | 15 | Ex. |
| 4 | 12 | 4 | 5 | 5 | 4 | 6 | 4 | 5 | 6 | 7 | 5 | Ex. |
| 5 | 8 | 5 | 6 | 8 | 6 | 4 | 5 | 6 | 15 | 15 | 18 | Ex. |
| 6 | 6 | 6 | 16 | 15 | 13 | 14 | 15 | 16 | 17 | 18 | 18 | Ex. |
| 7 | 12 | 6 | 6 | 6 | 7 | 6 | 5 | 4 | 4 | 4 | 5 | Ex. |
| 8 | 4 | 5 | 16 | 16 | 18 | 17 | 16 | 18 | 18 | 18 | 18 | Ex. |
| 9 | 12 | 16 | 18 | 20 | 18 | 20 | 19 | 18 | 17 | 16 | 17 | Ex. |
| 10 | 12 | 18 | 17 | 16 | 15 | 17 | 18 | 15 | 16 | 18 | 20 | Ex. |

*The ratio of increase in magnetic flux density of non-machining-affected zone $B_I$ to increase in mean magnetic flux density $B_0$.

It can be seen from Table 10 that in all of our examples, the error in prediction accuracy is 20% or lower, indicating that the iron loss can be predicted with high accuracy. In particular, it will be appreciated that for Examples No. 4 and 7 in which all the parameters were set under suitable conditions, the error in prediction accuracy is 10% or lower in every magnetic flux density region, where the iron loss can be predicted with very high accuracy.

In contrast, significant errors can be found in every magnetic flux density region for Comparative Example No. 1 in which the iron loss of a sample sheared to a width of 30 mm as measured in accordance with JIS C 2550 was applied as the predicted value without considering the influence of the machining strain.

The invention claimed is:

1. A method for predicting iron loss of a non-oriented electrical steel sheet after shearing to a certain width so that the non-oriented electrical steel sheet comprises a non-machining-affected zone in which no machining strain is introduced and a machining affected zone in which machining strain is introduced, the method comprising:

estimating the iron loss of the non-oriented electrical steel sheet after shearing $Wt(B_0)$ based on iron loss in the non-machining-affected zone $Wn(B_1)$ and iron loss in the machining affected zone $Wi(B_2)$ according to the following equation:

$$Wt(B_0)=Wn(B_1)*[\text{a width ratio of the non-machining-affected zone}]+Wi(B_2)*[\text{a width ratio of the machining affected zone}]$$

where $B_0$, $B_1$, and $B_2$ respectively denote a mean magnetic flux density of the non-oriented electrical steel sheet after shearing, a magnetic flux density of the non-machining-affected zone, and a magnetic flux density of the machining affected zone, upon excitation of the non-oriented electrical steel sheet after shearing, and where the width ratio of the non-machining-affected zone and the width ratio of the machining affected zone are a ratio of a total width of the non-machining-affected zone, and alternatively a ratio of a total width of the machining affected zone, to an entire width of the non-oriented electrical steel sheet after shearing, respectively, wherein the iron loss $Wi(B_2)$ of the machining affected zone is set based on iron loss of a sample having a width of 15 mm or less and iron loss of a sample having a width of 30 mm or more, both sheared from a steel sheet of the same material as the non-oriented electrical steel sheet by deriving the iron loss $Wi(B_2)$ by the following equation:

$$Wi(B_2)=(W_{s1}(B_0)-W_{s2}(B_1))*[\text{a width ratio of the non-machining-affected zone of the sample having a width of 30 mm or more}]/[\text{a width ratio of the machining affected zone of the sample having a width of 15 mm or less}]$$

where $W_{s1}(B_0)$ denotes the iron loss of the sample having a width of 15 mm or less and $W_{s2}(B_1)$ denotes the iron loss of the sample having a width of 30 mm or more, and where the width ratio of the non-machining-affected zone in the sample having a width of 30 mm or more is a ratio of a total width of the non-machining-affected zone to an entire width of the sample, and the width ratio of the machining affected zone of the sample having a width of 15 mm or less is a ratio of a total width of the machining affected zone to the entire width of the sample, or wherein as the iron loss $Wi(B_2)$ of the machining affected zone, iron loss as measured upon a uniaxial compressive stress of 100 MPa or more being applied to a steel sheet of the same material as the non-oriented electrical steel sheet is used.

2. The method for predicting iron loss of the non-oriented electrical steel sheet after shearing according to claim 1, wherein as the iron loss $Wn(B_1)$ of the non-machining-affected zone, iron loss of a sample having a width of 30 mm or more which is sheared from a steel sheet of the same material as the non-oriented electrical steel sheet is used.

3. The method for predicting iron loss of the non-oriented electrical steel sheet after shearing according to claim 1, wherein the iron loss $Wi(B_2)$ of the machining affected zone is set based on iron loss of a sample having a width of 15 mm or less and iron loss of a sample having a width of 30 mm or more, both sheared from a steel sheet of the same material as the non-oriented electrical steel sheet by deriving the iron loss $Wi(B_2)$ by the following equation:

$$Wi(B_2)=(W_{s1}(B_0)-W_{s2}(B_1))*[\text{a width ratio of the non-machining-affected zone of the sample having a width of 30 mm or more}]/[\text{a width ratio of the machining affected zone of the sample having a width of 15 mm or less}]$$

where $W_{s1}(B_0)$ denotes the iron loss of the sample having a width of 15 mm or less and $W_{s2}(B_1)$ denotes the iron loss of the sample having a width of 30 mm or more, and where the width ratio of the non-machining-affected zone in the sample having a width of 30 mm or more is a ratio of a total width of the non-machining-affected zone to an entire width of the sample, and the width ratio of the machining affected zone of the sample having a width of 15 mm or less is a ratio of a total width of the machining affected zone to the entire width of the sample.

4. The method for predicting iron loss of the non-oriented electrical steel sheet after shearing according to claim 1, wherein as the iron loss $Wi(B_2)$ of the machining affected zone, iron loss as measured upon a uniaxial compressive stress of 100 MPa or more being applied to the steel sheet of the same material as the non-oriented electrical steel sheet is used.

5. The method for predicting iron loss of the non-oriented electrical steel sheet after shearing according to claim 1, wherein the total width of the machining affected zone of the non-oriented electrical steel sheet after shearing is set to be two to four times a sheet thickness t of the non-oriented electrical steel sheet after shearing.

6. The method for predicting iron loss of the non-oriented electrical steel sheet after shearing according to claim 1, wherein a relationship between the mean magnetic flux density $B_0$ and the magnetic flux densities $B_1$, $B_2$ is set for each of the regions defined as Regions 1 to 3 below according to a value of the mean magnetic flux density $B_0$, and based on the setting, a value of the magnetic flux density $B_1$ and a value of the magnetic flux density $B_2$ for each region are derived:

Region 1 is a region in which as the mean magnetic flux density $B_0$ increases, the magnetic flux density of the non-machining-affected zone $B_1$ and the magnetic flux density of the machining affected zone $B_2$ increase at the same rate;

Region 2 is a region in which as the mean magnetic flux density $B_0$ increases, the magnetic flux density of the non-machining-affected zone $B_1$ increases at a higher rate than the magnetic flux density of the machining affected zone $B_2$; and Region 3 is a region in which as the mean magnetic flux density $B_0$ increases, the magnetic flux density of the machining affected zone $B_2$ increases at a higher rate than the magnetic flux density of the non-machining-affected zone $B_1$.

7. The method for predicting iron loss of the non-oriented electrical steel sheet after shearing according to claim 6, wherein a range in which the mean magnetic flux density $B_0$ ranges from 0 T to $B_a$ T is set as the Region 1, and $B_{as}$ is derived as a reference value for $B_a$ according to a sheet thickness t of the non-oriented electrical steel sheet after shearing from the following equations, and $B_a$ is selected in a range of the reference value $B_{as} \pm 0.2$ T (where $B_a \geq 0$ T):

$B_{as}$=0 (for $t \leq 0.25$ mm), $B_{as}$=1.2*$t$−0.3 (for 0.25 mm<$t \leq 0.50$ mm), and $B_{as}$=0.3 (for 0.5 mm<$t$).

8. The method for predicting iron loss of the non-oriented electrical steel sheet after shearing according to claim 6, wherein an upper limit $B_b$ for the mean magnetic flux density $B_0$ in the Region 2 is selected in a range of 1.45±0.15 T, and a ratio of increase in the magnetic flux density $B_1$ to increase in the mean magnetic flux density $B_0$ in the Region 2 is set to 1.02±0.015.

9. The method for predicting iron loss of the non-oriented electrical steel sheet after shearing according to claim 6, wherein an upper limit $B_c$ for the mean magnetic flux density $B_0$ in the Region 3 is set to a value that is taken by the mean magnetic flux density $B_0$ when the magnetic flux density $B_1$ is equal to the magnetic flux density $B_2$, and a ratio of increase in the magnetic flux density $B_1$ to increase in the mean magnetic flux density $B_0$ in the Region 3 is set to 0.93±0.02.

10. The method for predicting iron loss of the non-oriented electrical steel sheet after shearing according to claim 6, wherein a range in which the value of the mean magnetic flux density $B_0$ is greater than an upper limit $B_c$ for the mean magnetic flux density $B_0$ in the Region 3 is set as the Region 1.

* * * * *